United States Patent
Tran et al.

(10) Patent No.: US 9,271,806 B2
(45) Date of Patent: Mar. 1, 2016

(54) ADJUSTABLE FOOT PEDAL CONTROL FOR OPHTHALMIC SURGERY

(71) Applicant: Abbott Medical Optics Inc., Santa Ana, CA (US)

(72) Inventors: Tuan M Tran, Stanton, CA (US); James Gerg, Lake Forest, CA (US)

(73) Assignee: Abbott Medical Optics Inc., Santa Ana, CA (US)

(*) Notice: Subject to any disclaimer, the term of this patent is extended or adjusted under 35 U.S.C. 154(b) by 55 days.

(21) Appl. No.: 14/157,894

(22) Filed: Jan. 17, 2014

(65) Prior Publication Data

US 2014/0135785 A1   May 15, 2014

Related U.S. Application Data

(63) Continuation of application No. 12/613,562, filed on Nov. 6, 2009, now Pat. No. 8,749,188.

(60) Provisional application No. 61/112,210, filed on Nov. 7, 2008.

(51) Int. Cl.
   *B60L 15/12*  (2006.01)
   *A61B 19/00*  (2006.01)
   (Continued)

(52) U.S. Cl.
   CPC .............. *A61B 19/56* (2013.01); *A61F 9/00745* (2013.01); *A61F 9/00754* (2013.01);
   (Continued)

(58) Field of Classification Search
   CPC .................. A61B 2017/00973; H01H 21/245; H01H 3/14; Y10T 74/20888; Y10T 74/20894; Y10T 74/20528
   USPC .................................. 318/545, 549; 606/1, 4
   See application file for complete search history.

(56) References Cited

U.S. PATENT DOCUMENTS 1,848,024 A   3/1932 Owen
2,123,781 A   7/1938 Huber
(Continued)

FOREIGN PATENT DOCUMENTS

AU   2006235983 A1   5/2007
DE      3826414 A1   2/1989
(Continued)

OTHER PUBLICATIONS

Boyd, "Preparing for the Transition" in: The Art and the Science of Cataract Surgery, Chapter 7, 2001, pp. 93-133.
(Continued)

*Primary Examiner* — Rina Duda
(74) *Attorney, Agent, or Firm* — Abbott Medical Optics Inc.

(57) ABSTRACT

A foot pedal control for a surgical system, e.g., an ophthalmic surgery system, that adjusts to a number of different sizes of user's shoes. The foot pedal control has a treadle on which a user places his or her foot and a sensor that tracks the movements thereof. Adjustable lateral guides mount to the treadle and conform to both sides of the foot. The guides are shaped and positioned to conform to a wide variety of feet or shoes, and may easily be adjusted between users. A retractable heel stop converts between up for reference and down to enhance movement of the user's foot. A convertible handle may be stowed in a down position parallel to a base or pivoted up over the treadle for protection and ease of movement of the foot pedal control. The foot pedal control may be wireless and have various other electronic controls, and may have a dual-control treadle.

17 Claims, 16 Drawing Sheets

(51) Int. Cl.
*H01H 21/26* (2006.01)
*A61F 9/007* (2006.01)

(52) U.S. Cl.
CPC ............ *H01H21/26* (2013.01); *A61F 9/00736* (2013.01); *H01H 2300/014* (2013.01); *Y10T 74/20528* (2015.01)

(56) References Cited

U.S. PATENT DOCUMENTS

| | | |
|---|---|---|
| 3,076,904 A | 2/1963 | Claus et al. |
| 3,116,697 A | 1/1964 | Bilichniansky |
| 3,439,680 A | 4/1969 | Thomas, Jr. |
| 3,526,219 A | 9/1970 | Balamuth |
| 3,781,142 A | 12/1973 | Zweig |
| 3,857,387 A | 12/1974 | Shock |
| 4,017,828 A | 4/1977 | Watanabe et al. |
| 4,037,491 A | 7/1977 | Newbold |
| 4,189,286 A | 2/1980 | Murry et al. |
| 4,193,004 A | 3/1980 | Lobdell et al. |
| 4,276,023 A | 6/1981 | Phillips et al. |
| 4,537,561 A | 8/1985 | Xanthopoulos |
| 4,564,342 A | 1/1986 | Weber et al. |
| 4,590,934 A | 5/1986 | Malis et al. |
| 4,665,621 A | 5/1987 | Ackerman et al. |
| 4,706,687 A | 11/1987 | Rogers et al. |
| 4,757,814 A | 7/1988 | Wang et al. |
| 4,758,220 A | 7/1988 | Sundblom et al. |
| 4,772,263 A | 9/1988 | Dorman et al. |
| 4,773,897 A | 9/1988 | Scheller et al. |
| 4,818,186 A | 4/1989 | Pastrone et al. |
| 4,837,857 A | 6/1989 | Scheller et al. |
| 4,920,336 A | 4/1990 | Meijer |
| 4,921,477 A | 5/1990 | Davis |
| 4,933,843 A | 6/1990 | Scheller et al. |
| 4,954,960 A | 9/1990 | Lo et al. |
| 4,961,424 A | 10/1990 | Kubota et al. |
| 4,965,417 A | 10/1990 | Massie |
| 4,983,901 A | 1/1991 | Lehmer |
| 4,998,972 A | 3/1991 | Chin et al. |
| 5,006,110 A | 4/1991 | Garrison et al. |
| 5,020,535 A | 6/1991 | Parker et al. |
| 5,026,387 A | 6/1991 | Thomas |
| 5,039,973 A | 8/1991 | Carballo |
| 5,091,656 A | 2/1992 | Gahn |
| 5,108,367 A | 4/1992 | Epstein et al. |
| 5,110,270 A | 5/1992 | Morrick |
| 5,125,891 A | 6/1992 | Hossain et al. |
| 5,160,317 A | 11/1992 | Costin |
| 5,195,960 A | 3/1993 | Hossain et al. |
| 5,195,961 A | 3/1993 | Takahashi et al. |
| 5,195,971 A | 3/1993 | Sirhan |
| 5,230,614 A | 7/1993 | Zanger et al. |
| 5,249,121 A | 9/1993 | Baum et al. |
| 5,268,624 A | 12/1993 | Zanger |
| 5,271,379 A | 12/1993 | Phan et al. |
| 5,282,787 A | 2/1994 | Wortrich |
| 5,323,543 A | 6/1994 | Steen et al. |
| 5,342,293 A | 8/1994 | Zanger |
| 5,350,357 A | 9/1994 | Kamen et al. |
| 5,351,676 A | 10/1994 | Putman |
| 5,388,569 A | 2/1995 | Kepley |
| 5,454,783 A | 10/1995 | Grieshaber et al. |
| 5,464,391 A | 11/1995 | DeVale |
| 5,470,211 A | 11/1995 | Knott et al. |
| 5,470,312 A | 11/1995 | Zanger et al. |
| 5,499,969 A | 3/1996 | Beuchat et al. |
| 5,520,652 A | 5/1996 | Peterson |
| 5,533,976 A | 7/1996 | Zaleski et al. |
| 5,549,461 A | 8/1996 | Newland |
| 5,554,894 A | 9/1996 | Sepielli |
| 5,561,575 A | 10/1996 | Eways |
| 5,569,188 A | 10/1996 | Mackool |
| 5,580,347 A | 12/1996 | Reimels |
| 5,591,127 A | 1/1997 | Barwick et al. |
| 5,653,887 A | 8/1997 | Wahl et al. |
| 5,657,000 A | 8/1997 | Ellingboe |
| 5,676,530 A | 10/1997 | Nazarifar |
| 5,676,649 A | 10/1997 | Boukhny et al. |
| 5,676,650 A | 10/1997 | Grieshaber et al. |
| 5,693,020 A | 12/1997 | Rauh |
| 5,697,898 A | 12/1997 | Devine |
| 5,697,910 A | 12/1997 | Cole et al. |
| 5,700,240 A | 12/1997 | Barwick et al. |
| 5,724,264 A | 3/1998 | Rosenberg et al. |
| 5,728,130 A | 3/1998 | Ishikawa et al. |
| 5,733,256 A | 3/1998 | Costin |
| 5,745,647 A | 4/1998 | Krause |
| 5,747,824 A | 5/1998 | Jung et al. |
| 5,777,602 A | 7/1998 | Schaller et al. |
| 5,805,998 A | 9/1998 | Kodama |
| 5,807,075 A | 9/1998 | Jacobsen et al. |
| 5,810,766 A | 9/1998 | Barnitz et al. |
| 5,830,176 A | 11/1998 | Mackool |
| 5,843,109 A | 12/1998 | Mehta et al. |
| 5,859,642 A | 1/1999 | Jones |
| 5,871,492 A | 2/1999 | Sorensen |
| 5,879,298 A | 3/1999 | Drobnitzky et al. |
| 5,883,615 A | 3/1999 | Fago et al. |
| 5,899,674 A | 5/1999 | Jung et al. |
| 5,928,257 A | 7/1999 | Kablik et al. |
| 5,983,749 A | 11/1999 | Holtorf |
| 6,002,484 A | 12/1999 | Rozema et al. |
| 6,024,428 A | 2/2000 | Uchikata |
| 6,062,829 A | 5/2000 | Ognier |
| 6,077,285 A | 6/2000 | Boukhny |
| 6,086,598 A | 7/2000 | Appelbaum et al. |
| 6,109,895 A | 8/2000 | Ray et al. |
| 6,117,126 A | 9/2000 | Appelbaum et al. |
| 6,139,320 A | 10/2000 | Hahn |
| 6,150,623 A | 11/2000 | Chen |
| 6,179,829 B1 | 1/2001 | Bisch et al. |
| 6,219,032 B1 | 4/2001 | Rosenberg et al. |
| 6,251,113 B1 | 6/2001 | Appelbaum et al. |
| 6,260,434 B1 | 7/2001 | Holtorf |
| 6,360,630 B2 | 3/2002 | Holtorf |
| 6,368,269 B1 | 4/2002 | Lane |
| 6,411,062 B1 | 6/2002 | Baranowski et al. |
| 6,424,124 B2 | 7/2002 | Ichihara et al. |
| 6,436,072 B1 | 8/2002 | Kullas et al. |
| 6,452,120 B1 | 9/2002 | Chen |
| 6,452,123 B1 | 9/2002 | Chen |
| 6,491,661 B1 | 12/2002 | Boukhny et al. |
| 6,511,454 B1 | 1/2003 | Nakao et al. |
| 6,537,445 B2 | 3/2003 | Muller |
| 6,595,948 B2 | 7/2003 | Suzuki et al. |
| 6,632,214 B2 | 10/2003 | Morgan et al. |
| 6,674,030 B2 | 1/2004 | Chen et al. |
| 6,830,555 B2 | 12/2004 | Rockley et al. |
| 6,852,092 B2 | 2/2005 | Kadziauskas et al. |
| 6,862,951 B2 | 3/2005 | Peterson et al. |
| 6,908,451 B2 | 6/2005 | Brody et al. |
| 6,962,488 B2 | 11/2005 | Davis et al. |
| 6,962,581 B2 | 11/2005 | Thoe |
| 7,011,761 B2 | 3/2006 | Muller |
| 7,012,203 B2 | 3/2006 | Hanson et al. |
| 7,070,578 B2 | 7/2006 | Leukanech et al. |
| 7,073,083 B2 | 7/2006 | Litwin, Jr. et al. |
| 7,087,049 B2 | 8/2006 | Nowlin et al. |
| 7,103,344 B2 | 9/2006 | Menard |
| 7,167,723 B2 | 1/2007 | Zhang |
| 7,169,123 B2 | 1/2007 | Kadziauskas et al. |
| 7,236,766 B2 | 6/2007 | Freeburg |
| 7,236,809 B2 | 6/2007 | Fischedick et al. |
| 7,242,765 B2 | 7/2007 | Hairston |
| 7,244,240 B2 | 7/2007 | Nazarifar et al. |
| 7,289,825 B2 | 10/2007 | Fors et al. |
| 7,300,264 B2 | 11/2007 | Souza |
| 7,316,664 B2 | 1/2008 | Kadziauskas et al. |
| 7,336,976 B2 | 2/2008 | Ito |
| 7,381,917 B2 | 6/2008 | Dacquay et al. |
| 7,439,463 B2 | 10/2008 | Brenner et al. |
| 7,465,285 B2 | 12/2008 | Hutchinson et al. |
| 7,470,277 B2 | 12/2008 | Finlay et al. |

(56) References Cited

U.S. PATENT DOCUMENTS

| | | |
|---|---|---|
| 7,526,038 B2 | 4/2009 | McNamara |
| 7,591,639 B2 | 9/2009 | Kent |
| 7,731,484 B2 | 6/2010 | Yamamoto et al. |
| 7,776,006 B2 | 8/2010 | Childers et al. |
| 7,811,255 B2 | 10/2010 | Boukhny et al. |
| 7,883,521 B2 | 2/2011 | Rockley et al. |
| 7,921,017 B2 | 4/2011 | Claus et al. |
| 7,967,777 B2 | 6/2011 | Edwards et al. |
| 8,070,712 B2 | 12/2011 | Muri et al. |
| 8,075,468 B2 | 12/2011 | Min et al. |
| 2001/0023331 A1 | 9/2001 | Kanda et al. |
| 2001/0047166 A1 | 11/2001 | Wuchinich |
| 2001/0051788 A1 | 12/2001 | Paukovits et al. |
| 2002/0019215 A1 | 2/2002 | Romans |
| 2002/0019607 A1 | 2/2002 | Bui |
| 2002/0045887 A1 | 4/2002 | DeHoogh et al. |
| 2002/0070840 A1 | 6/2002 | Fischer et al. |
| 2002/0098859 A1 | 7/2002 | Murata |
| 2002/0137007 A1 | 9/2002 | Beerstecher |
| 2002/0179462 A1 | 12/2002 | Silvers |
| 2003/0028091 A1 | 2/2003 | Simon et al. |
| 2003/0083016 A1 | 5/2003 | Evans et al. |
| 2003/0108429 A1 | 6/2003 | Angelini et al. |
| 2003/0125717 A1 | 7/2003 | Whitman |
| 2003/0224729 A1 | 12/2003 | Arnold |
| 2003/0226091 A1 | 12/2003 | Platenberg et al. |
| 2004/0037724 A1 | 2/2004 | Haser et al. |
| 2004/0193182 A1 | 9/2004 | Yaguchi et al. |
| 2004/0212344 A1 | 10/2004 | Tamura et al. |
| 2004/0215127 A1 | 10/2004 | Kadziauskas et al. |
| 2004/0224641 A1 | 11/2004 | Sinn |
| 2004/0253129 A1 | 12/2004 | Sorensen et al. |
| 2005/0039567 A1* | 2/2005 | Peterson et al. ............... 74/561 |
| 2005/0054971 A1 | 3/2005 | Steen et al. |
| 2005/0069419 A1 | 3/2005 | Cull et al. |
| 2005/0070859 A1 | 3/2005 | Cull et al. |
| 2005/0095153 A1 | 5/2005 | Demers et al. |
| 2005/0103607 A1* | 5/2005 | Mezhinsky ............... 200/86.5 |
| 2005/0109595 A1* | 5/2005 | Mezhinsky et al. ........ 200/86.5 |
| 2005/0118048 A1 | 6/2005 | Traxinger |
| 2005/0130098 A1 | 6/2005 | Warner |
| 2005/0187513 A1 | 8/2005 | Rabiner et al. |
| 2005/0197131 A1 | 9/2005 | Ikegami |
| 2005/0236936 A1 | 10/2005 | Shiv et al. |
| 2005/0245888 A1 | 11/2005 | Cull |
| 2005/0261628 A1 | 11/2005 | Boukhny et al. |
| 2006/0035585 A1 | 2/2006 | Washiro |
| 2006/0036180 A1 | 2/2006 | Boukhny et al. |
| 2006/0041220 A1 | 2/2006 | Boukhny et al. |
| 2006/0046659 A1 | 3/2006 | Haartsen et al. |
| 2006/0074405 A1 | 4/2006 | Malackowski et al. |
| 2006/0078448 A1 | 4/2006 | Holden |
| 2006/0114175 A1 | 6/2006 | Boukhny |
| 2006/0145540 A1* | 7/2006 | Mezhinsky ............... 307/119 |
| 2006/0219049 A1* | 10/2006 | Horvath et al. ............... 74/560 |
| 2006/0219962 A1 | 10/2006 | Dancs et al. |
| 2006/0224107 A1 | 10/2006 | Claus et al. |
| 2006/0236242 A1 | 10/2006 | Boukhny et al. |
| 2007/0016174 A1 | 1/2007 | Millman et al. |
| 2007/0049898 A1 | 3/2007 | Hopkins et al. |
| 2007/0060926 A1 | 3/2007 | Escaf |
| 2007/0073214 A1 | 3/2007 | Dacquay et al. |
| 2007/0073309 A1 | 3/2007 | Kadziauskas et al. |
| 2007/0078379 A1 | 4/2007 | Boukhny et al. |
| 2007/0249942 A1 | 10/2007 | Salehi et al. |
| 2008/0033342 A1 | 2/2008 | Staggs |
| 2008/0066542 A1 | 3/2008 | Gao |
| 2008/0112828 A1 | 5/2008 | Muri et al. |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1 | 5/2008 | Muri et al. |
| 2008/0114312 A1 | 5/2008 | Muri et al. |
| 2008/0114387 A1 | 5/2008 | Hertweck et al. |
| 2008/0125695 A1 | 5/2008 | Hopkins et al. |
| 2008/0125697 A1 | 5/2008 | Gao |
| 2008/0125698 A1 | 5/2008 | Gerg et al. |
| 2008/0129695 A1 | 6/2008 | Li |
| 2008/0146989 A1 | 6/2008 | Zacharias |
| 2008/0243105 A1 | 10/2008 | Horvath |
| 2008/0262476 A1 | 10/2008 | Krause et al. |
| 2008/0281253 A1 | 11/2008 | Injev et al. |
| 2008/0294087 A1 | 11/2008 | Steen et al. |
| 2008/0312594 A1 | 12/2008 | Urich et al. |
| 2009/0005712 A1 | 1/2009 | Raney |
| 2009/0005789 A1 | 1/2009 | Charles |
| 2009/0048607 A1 | 2/2009 | Rockley |
| 2009/0163853 A1 | 6/2009 | Cull et al. |
| 2010/0036256 A1 | 2/2010 | Boukhny et al. |
| 2010/0185150 A1 | 7/2010 | Zacharias |
| 2010/0280435 A1 | 11/2010 | Raney et al. |
| 2011/0092887 A1 | 4/2011 | Wong et al. |
| 2011/0092924 A1 | 4/2011 | Wong et al. |
| 2011/0092962 A1 | 4/2011 | Ma et al. |
| 2011/0098721 A1 | 4/2011 | Tran et al. |
| 2011/0160646 A1 | 6/2011 | Kadziauskas et al. |
| 2012/0065580 A1 | 3/2012 | Gerg et al. |

FOREIGN PATENT DOCUMENTS

| | | |
|---|---|---|
| EP | 56019 A1 | 7/1982 |
| EP | 619993 A1 | 10/1994 |
| EP | 1010437 A1 | 6/2000 |
| EP | 1072285 A1 | 1/2001 |
| EP | 1113562 A1 | 7/2001 |
| EP | 1310267 A2 | 5/2003 |
| EP | 1469440 A2 | 10/2004 |
| EP | 1550406 A2 | 7/2005 |
| EP | 1704839 A1 | 9/2006 |
| EP | 1779879 A1 | 5/2007 |
| EP | 1787606 A1 | 5/2007 |
| EP | 1849443 A1 | 10/2007 |
| EP | 1849444 A1 | 10/2007 |
| EP | 1857128 A1 | 11/2007 |
| EP | 1867349 A1 | 12/2007 |
| EP | 1310267 B1 | 1/2008 |
| EP | 1873501 A1 | 1/2008 |
| EP | 1900347 A1 | 3/2008 |
| EP | 1925274 A2 | 5/2008 |
| EP | 1867349 B1 | 11/2008 |
| ES | 2264369 A1 | 12/2006 |
| GB | 2230301 A | 10/1990 |
| GB | 2352887 A | 2/2001 |
| JP | S5724482 A | 2/1982 |
| JP | 2008188110 A | 8/2008 |
| WO | WO-9220310 A1 | 11/1992 |
| WO | WO-9315777 A2 | 8/1993 |
| WO | WO-9317729 A1 | 9/1993 |
| WO | WO-9324082 A1 | 12/1993 |
| WO | WO-9405346 A1 | 3/1994 |
| WO | WO-9632144 A1 | 10/1996 |
| WO | WO-9818507 A1 | 5/1998 |
| WO | WO-9917818 A1 | 4/1999 |
| WO | WO-0000096 A1 | 1/2000 |
| WO | WO-0070225 A1 | 11/2000 |
| WO | WO-0122696 A1 | 3/2001 |
| WO | WO-0228449 A2 | 4/2002 |
| WO | WO-0234314 A1 | 5/2002 |
| WO | WO-03102878 A1 | 12/2003 |
| WO | WO-2004096360 A1 | 11/2004 |
| WO | WO-2004114180 A1 | 12/2004 |
| WO | Wo-2005084728 A2 | 9/2005 |
| WO | WO-2005092023 A2 | 10/2005 |
| WO | WO-2005092047 A2 | 10/2005 |
| WO | WO-2006101908 A2 | 9/2006 |
| WO | WO-2006125280 A1 | 11/2006 |
| WO | WO-2007121144 A1 | 10/2007 |
| WO | WO-2007143677 A2 | 12/2007 |
| WO | WO-2007143797 A1 | 12/2007 |
| WO | WO-2007149637 A2 | 12/2007 |
| WO | WO-2008030872 A1 | 3/2008 |
| WO | WO-2008060859 A1 | 5/2008 |
| WO | WO-2008060902 A1 | 5/2008 |
| WO | WO-2008060995 A1 | 5/2008 |

(56) References Cited

FOREIGN PATENT DOCUMENTS

| WO | WO-2010054146 A1 | 5/2010 |
|----|------------------|--------|
| WO | WO-2010054225 A2 | 5/2010 |
| WO | WO-2013142009 A1 | 9/2013 |

OTHER PUBLICATIONS

Co-pending U.S. Appl. No. 13/922,475, filed Jun. 20, 2013.
Definition of "Parameter", Retrieved from the Internet:< URL: http://dictionary.reference.com/browse/parameter>.
English Human Translation of JP57024482 from Feb. 9, 1982.
European Search Report for Application No. EP10164058, mailed on Jun. 25, 2010, 2 pages.
European Search Report for Application No. EP13184138.9, mailed on Oct. 24, 2013, 7 pages.
Examination Report mailed Mar. 28, 2012 for European Application No. EP09791072 filed Jul. 31, 2009, 3 pages.
International Preliminary Report on Patentability and Written Opinion for Application No. PCT/US07/083875, mailed on May 12, 2009, 8 pages.
International Preliminary Report on Patentability and Written Opinion for Application No. PCT/US07/083880, mailed on May 12, 2009, 7 pages.
International Preliminary Report on Patentability and Written Opinion for Application No. PCT/US07/084157, mailed on May 12, 2009, 10 pages.
International Preliminary Report on Patentability and Written Opinion for Application No. PCT/US07/084163, mailed on May 12, 2009, 8 pages.
International Preliminary Report on Patentability and Written Opinion for Application No. PCT/US08/064240, mailed on Nov. 24, 2009, 7 pages.
International Preliminary Report on Patentability and Written Opinion for Application No. PCT/US2006/38978, mailed on Apr. 16, 2008, 8 pages.
International Preliminary Report on Patentability and Written Opinion for Application No. PCT/US2006/39868, mailed on Apr. 16, 2008, 6 pages.
International Preliminary Report on Patentability and Written Opinion for Application No. PCT/US2008/072974, mailed on Feb. 16, 2010, 6 pages.
International Preliminary Report on Patentability and Written Opinion for Application No. PCT/US2008/71704, mailed on Feb. 2, 2010, 8 pages.
International Preliminary Report on Patentability and Written Opinion for Application No. PCT/US2009/052473, mailed on Feb. 1, 2011, 7 pages.
International Preliminary Report on Patentability and Written Opinion for Application No. PCT/US2009/063479, mailed on May 10, 2011, 11 pages.
International Preliminary Report on Patentability and Written Opinion for Application No. PCT/US2009/063589, mailed on May 10, 2011, 12 pages.
International Search Report and Written Opinion for Application No. PCT/US2014/047055, mailed on Oct. 17, 2014, 11 pages.
International Search Report and Written Opinion, mailed Mar. 2, 2010, and International Preliminary Report on Patentability, mailed May 10, 2011, for Application No. PCT/US2009/063482, 13 pages.
International Search Report and Written Opinion, mailed Nov. 2, 2009, and International Preliminary Report on Patentability, mailed Feb. 1, 2011, for Application No. PCT/US2009/052466, 12 pages.
International Search Report and Written Opinion, mailed May 10, 2010, and International Preliminary Report on Patentability, mailed May 10, 2011, for Application No. PCT/US2009/063569, 17 pages.
International Search Report and Written Opinion, mailed Feb. 11, 2010, and International Preliminary Report on Patentability, mailed May 10, 2011, for Application No. PCT/US2009/063486, 13 pages.
International Search Report and Written Opinion, mailed Feb. 19, 2010, and International Preliminary Report on Patentability, mailed May 10, 2011, for Application No. PCT/US2009/63488, 9 pages.
International Search Report and Written Opinion, mailed Apr. 22, 2010, and International Preliminary Report on Patentability, mailed May 10, 2011, for Application No. PCT/US2009/063493, 8 pages.
International Search Report for Application No. PCT/US07/083875, mailed on May 7, 2008, 4 pages.
International Search Report for Application No. PCT/US07/083880, mailed on May 30, 2008, 4 pages.
International Search Report for Application No. PCT/US07/084157, mailed on Apr. 1, 2008, 3 pages.
International Search Report for Application No. PCT/US07/084163, mailed on Apr. 1, 2008, 3 pages.
International Search Report for Application No. PCT/US08/064240, mailed on Oct. 29, 2008, 3 pages.
International Search Report for Application No. PCT/US08/071704, mailed on Nov. 26, 2008, 3 pages.
International Search Report for Application No. PCT/US08/072974, mailed on Feb. 23, 2009, 2 pages.
International Search Report for Application No. PCT/US2006/38978, mailed on Feb. 27, 2007, 3 pages.
International Search Report for Application No. PCT/US2006/39868, mailed on Nov. 12, 2007, 3 pages.
International Search Report for Application No. PCT/US2009/052473, mailed on Nov. 2, 2009, 3 pages.
International Search Report for Application No. PCT/US2009/063479, mailed on Jun. 11, 2010, 5 pages.
International Search Report for Application No. PCT/US2009/063589, mailed on Jul. 21, 2010, 7 pages.
International Search Report for Application No. PCT/US2013/027728, mailed on Jul. 31, 2013, 9 pages.
Merritt R., et al., Wireless Nets Starting to link Medical Gear [online] 2004 [retrieved on Feb. 12, 2007]. Retrieved from the Internet: <http://www.embedded.com/news/embeddedindustry/17200577?_requestid=174370>.
Phacoemulsification, [online] [retrieved on Jul. 1, 2009]. Retrieved from the Internet: <http://en.wikipedia.org/wiki/Phacoemulsification>, 2 pages.

* cited by examiner

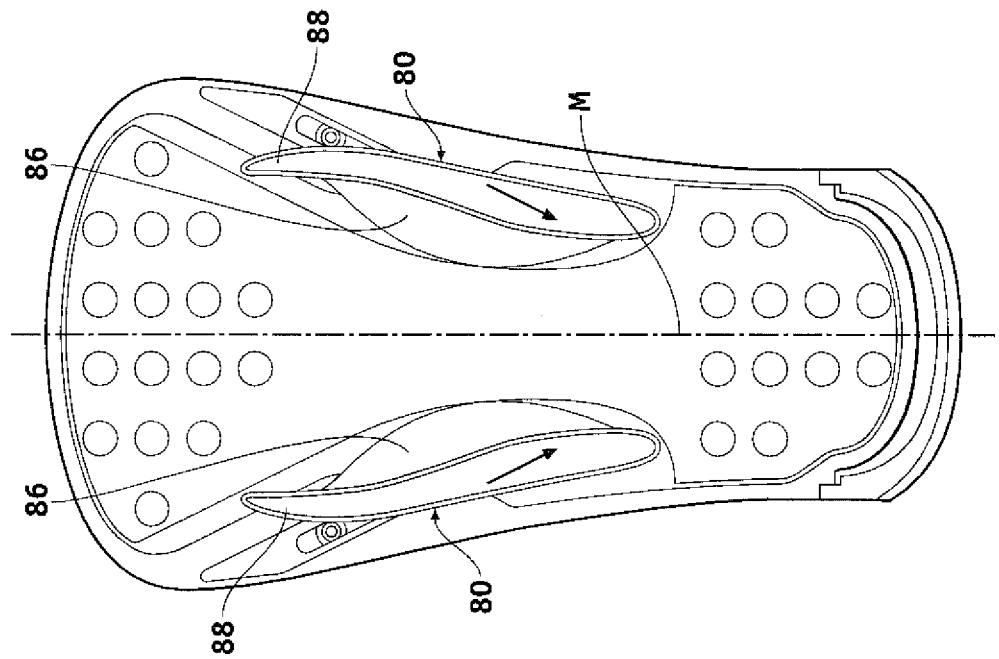
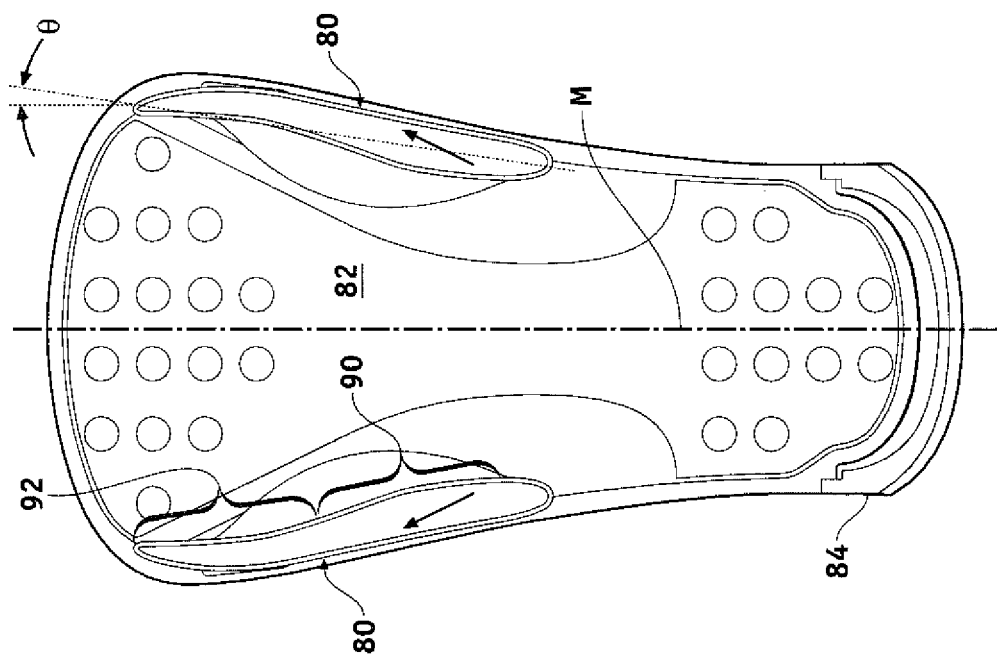

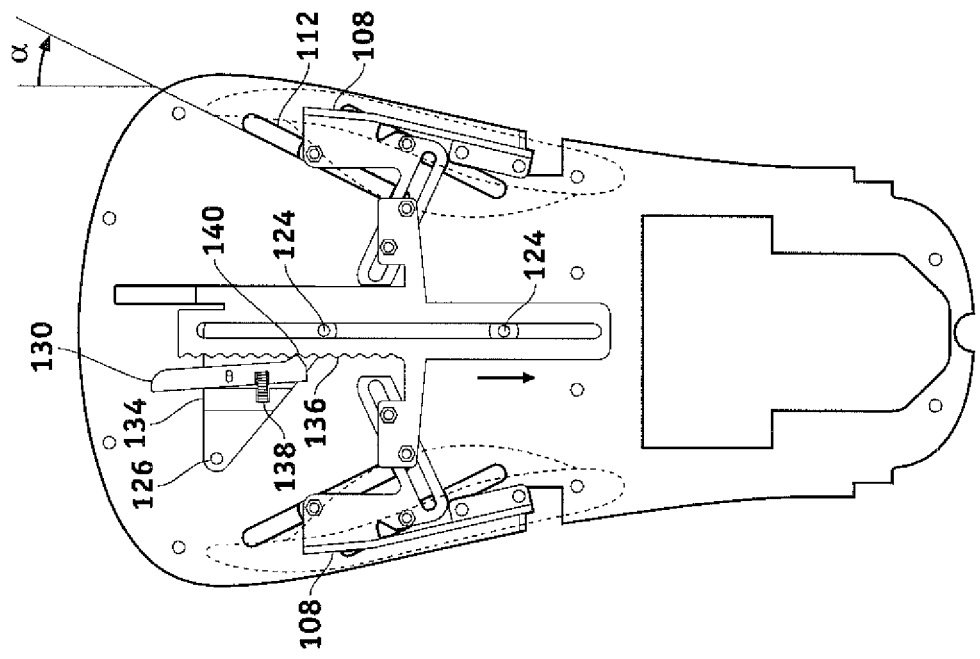
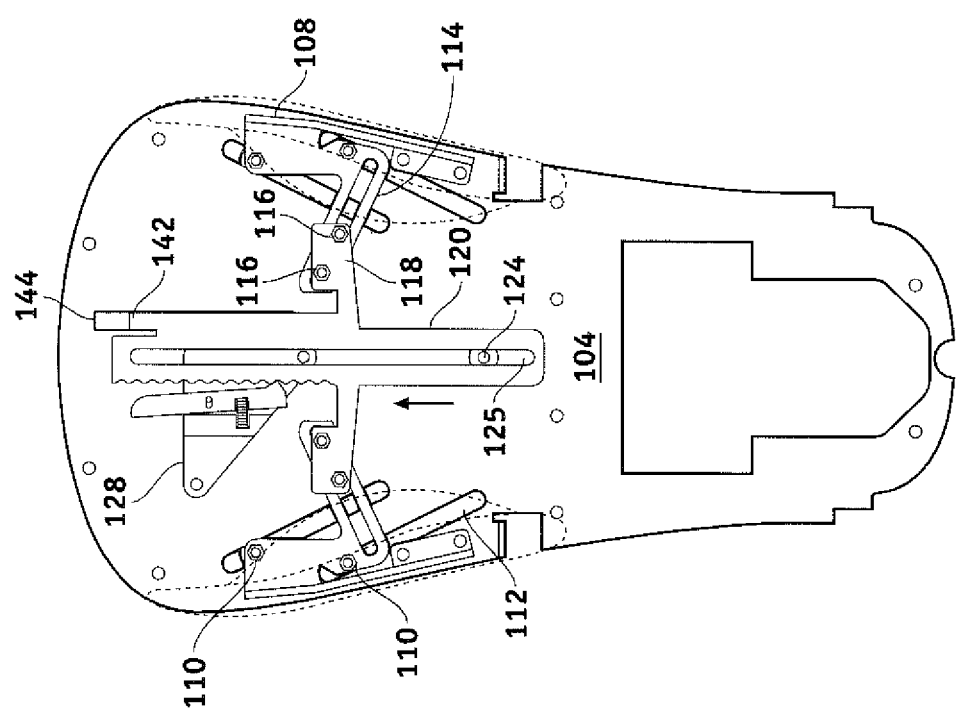

ADJUSTABLE FOOT PEDAL CONTROL FOR OPHTHALMIC SURGERY

This application is a continuation application and claims priority to U.S. application Ser. No. 12/613,562 filed on Nov. 6, 2009, which is a non-provisional of U.S. Provisional application No. 61/112,210 filed on Nov. 7, 2008, the entire contents of each are hereby incorporated by reference in their entirety for all purposes as if fully set forth herein.

FIELD OF THE INVENTION

The present application relates to operating controls for ophthalmic surgical apparatus and, more particularly, to an adjustable foot operated control.

BACKGROUND OF THE INVENTION

Ophthalmic surgical apparatus such as phacoemulsification apparatus typically include operating controls for regulating parameters or functions of the apparatus. Such phacoemulsification apparatus is particularly directed for surgically removing the natural, crystalline lenses from cataractic eyes prior to the insertion of an artificial intraocular lens.

Such apparatus typically includes a control cabinet, power supply, one or more pumps as well as associated electronic hardware for operating a multifunction handheld surgical implement in order to sonically emulsify eye tissue, irrigate the eye with a saline solution and aspirate the emulsified lens from the eye.

In view of the handheld instrumentation necessary for a phacoemulsification procedure, foot controls are frequently provided in order to facilitate use of the handpiece by delegating other control functions to the foot pedal device.

Any number of foot pedal device systems have been utilized which included a variety of pneumatic and electrical actuators to control the ophthalmic surgical apparatus. For instance, improved foot pedal control systems such as that described in U.S. Pat. No. 4,983,901 provide for a virtually unlimited number of control variations and modes for operating phacoemulsification apparatus. One popular type of foot control is termed a dual-control foot pedal because of the two directions of foot movement to actuate the controls. A treadle (the actual pedal) may be pivoted in a vertical plane, as in a standard car accelerator-type pedal, while also rotated in a horizontal plane or yaw direction. In addition to the dual treadle control, one or more other foot-actuated switches placed close to the treadle are often provided for easy access.

The foot pedal must be user friendly in order to provide a surgeon comfort and reliability in its use so as not to initiate disruption of the surgeon's concentration when performing surgery. During control of the foot pedal the surgeon's posture is influenced by efforts to prevent losing contact with the foot pedal, which is achieved by keeping one foot flexed above the pedal and loading the body weight on the other foot. This causes a non-ergonomic posture which can lead to physical discomfort, and sometimes mistakes in control of the foot pedal.

Furthermore, as may be expected, different types of foot pedals are preferred by different surgeons, with some surgeons preferring an accelerator-type pedal in which the sole of the surgeon's foot is utilized for depression, while others desire a pedal engageable by the surgeon's toe in order to depress the pedal. This, of course, leads to the development of a multitude of foot pedal devices of diverse configuration in order to provide the comfort and reliability desired by individual surgeons. For instance, U.S. Pat. No. 6,360,630 to Holtorf discloses a dual position foot pedal rotatably mounted to a base in order to be operated by the toe or sole of a user's foot. However, even with such flexible designs, a change in foot pedals is often required when phacoemulsification apparatus is utilized in sequence by different physicians, which is inconvenient and may require recalibration of the apparatus. In addition, such alternative foot pedals may not be available or even offered by a manufacturer.

Despite the availability of a number of relatively effective foot pedal designs, there is a need for a more ergonomically flexible foot pedal that enhances surgeon comfort and concentration.

BRIEF DESCRIPTION OF THE DRAWINGS

Features and advantages of the present invention will become appreciated as the same become better understood with reference to the specification, claims, and appended drawings wherein:

FIGS. 8A and 8B are top plan views of a treadle of the foot pedal control illustrating laterally-adjustable guides thereon;

FIGS. 12A and 12B are top plan views of actuation plate of the treadle with guides adjusted in two different positions;

SUMMARY OF THE INVENTION

Figure 1:
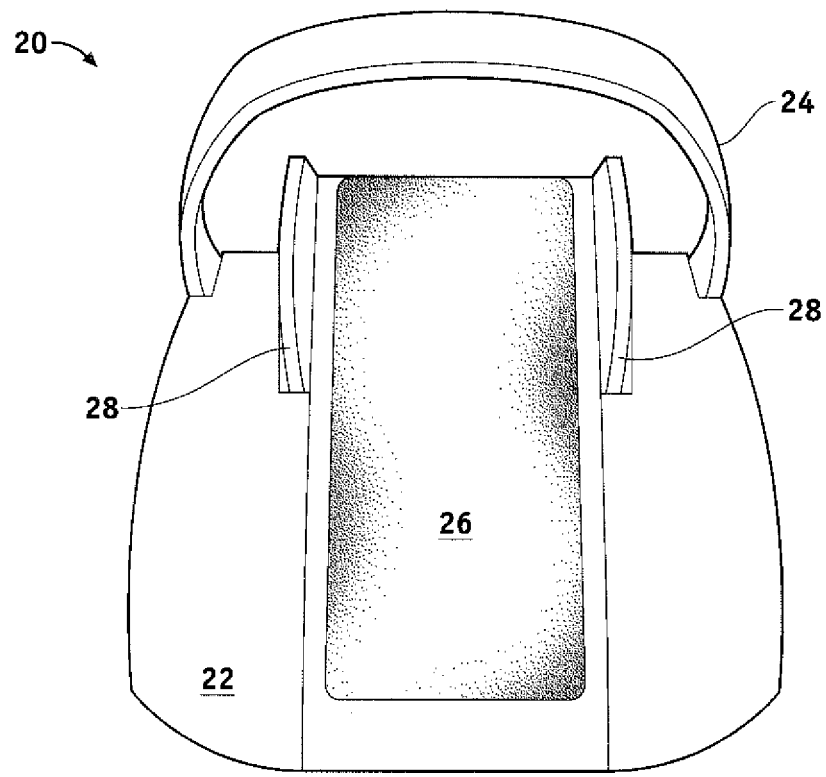
FIG. 1 is a top view of a prior art foot pedal control for ophthalmic surgery.

The present application discloses a foot pedal control for a surgical system (e.g., an ophthalmic surgery system) that adjusts to a number of different sizes of users' shoes. The foot pedal control has a treadle on which a user places his or her foot and a sensor that tracks the movements thereof. Adjustable lateral guides mount to the treadle and conform to both sides of the foot. The guides are shaped and positioned to conform to a wide variety of feet or shoes, and may easily be adjusted between users. A retractable heel stop converts between up for reference and down to enhance movement of the user's foot. A convertible handle may be stowed in a down position parallel to a base or pivoted up over the treadle for protection and ease of movement of the foot pedal control. The foot pedal control may be wireless and have various other electronic controls, and may have a dual-control treadle.

In accordance with one embodiment, a foot pedal control for a surgical system comprises a base, a treadle mounted for rotational yaw movement relative to the base and having a generally planar foot platform, and a sensor that tracks the yaw movements of the treadle and generates an electronic signal therefor. A pair of guides mounted on the treadle flank and extend upward from the foot platform, wherein at least one of the guides is movable to adjust the lateral spacing therebetween and accommodate variable foot widths on the foot platform therebetween.

In one embodiment, both of the guides are adjustable, and the guides may be adjustable independent of one another or move in tandem. The guides may each mount to articulate on the treadle with at least two adjustable segments. Preferably, both of the guides are also adjustable in an anterior-posterior direction, however at least one adjustable guide is preferably adjustable in an anterior-posterior direction and translates along an angled slot in the treadle. The angled slot desirably extends from a posterior point outward in an anterior direction at an angle of between about 15° and 45° from the longitudinal axis of the treadle. Further, the guide may be configured to move along the angled slot in a ratcheted fashion so as to have a series of stop positions distinguished by audible and/or tactile clicks.

The treadle may be a dual-motion treadle also mounted for vertical pivoting movement relative to the base, and the control further includes a sensor that tracks the pivoting movements and generates an electronic signal therefor. In one embodiment, the guides have a rail extending upward to a height generally perpendicular to the foot platform of between about 15 mm (0.6 inches) and 38 mm (1.5 inches). Desirably, the guides are elongated in an anterior-posterior direction and each includes a lip extending toward the other guide and generally parallel to the foot platform, and a rail extending upward from the lip generally perpendicular to the foot platform. The guides may be elongated in an anterior-posterior direction and S-shaped so as to have convex and concave inner faces to conform to different areas of users' feet. In one version, the treadle further includes a heel stop at the posterior end of the foot platform, the heel stop being convertible from a first position extending upward from the foot platform and a second position at or below the level of the foot platform.

Another aspect of the present application is a system for surgery including a surgery unit having a hand-held operative tip connected to a console. A foot pedal control in electronic communication with the console features a base and a treadle mounted for rotational yaw movement relative to the base and having a generally planar foot platform. The foot pedal control has a built-in sensor that tracks the yaw movements of the treadle and generates an electronic signal for communication to the console and subsequent control of the operative tip. The treadle has a pair of guides mounted thereon flanking and extending upward from the foot platform, wherein at least one of the guides is movable to adjust the lateral spacing therebetween and accommodate variable foot widths on the foot platform therebetween.

In one embodiment, the surgery unit is for ophthalmic surgery and the operative tip is adapted for insertion into an eye and includes a lumen for aspiration. Variations of the foot pedal control in the surgical system are described above.

Another system for surgery disclosed herein comprises a surgery unit including an operative tip connected to a console, and a foot pedal control in electronic communication with the console. The foot pedal control has a base with an undercarriage arranged to lie flat on a ground surface, and a treadle mounted for vertical pivoting movement relative to the base. The foot pedal control has a built-in sensor that tracks the pivoting movement of the treadle and generates an electronic signal for communication to the console and subsequent control of the operative tip. A carrying handle connects to the base and converts between at least two positions—a first position above the treadle and generally perpendicular to the undercarriage of the base, and a second position out of the way of the treadle and generally parallel to the undercarriage of the base.

In one embodiment, the surgery unit is for ophthalmic surgery and the operative tip is adapted for insertion into an eye and includes a lumen for aspiration. Variations of the foot pedal control in the surgical system are described above.

In one embodiment, the carrying handle is mounted to the base to lock into the two positions. Preferably, the carrying handle has two ends mounted to the base at two pivot points, and each pivot point features an actuator for unlocking the carrying handle for rotation, wherein both actuators must be activated to convert the carrying handle between positions. The carrying handle may mount to the base to pivot about an axis parallel but offset with respect to the plane defined by the undercarriage of the base, wherein in the first position above the treadle and generally perpendicular to the undercarriage of the base the carrying handle defines a curvilinear side strut that is convex in the anterior direction.

DETAILED DESCRIPTION OF THE PREFERRED EMBODIMENTS

The present application describes an improved foot pedal control for ophthalmic surgery that adjusts to a number of different sizes of users' shoes. An exemplary illustrated embodiment is designed for ophthalmic surgery, although the foot pedal control may be modified for other types of surgery, such as endoscopic coagulation surgery. Furthermore, the exemplary foot pedal is described as having a number of functional features, and it should be understood that some of these features may be amended or modified as needed. Likewise, though the illustrated design with an adjustable foot shape and movable handle is particularly well-suited for the controls shown, those controls may be modified while still retaining the novel aspects described herein.

To better understand the limitations of prior art foot pedal controls, two currently available models will be discussed. FIG. 1 is a top view of a foot pedal control 20 for ophthalmic surgery that is available as Model No. AMO SOV680701 from Advanced Medical Optics, Inc. of Santa Ana, Calif. The foot pedal control 20 includes a base 22 having an upstanding, generally inverted U-shaped carrying handle 24 thereon. A generally rectangular treadle 26 having a non-stick surface thereon is arranged to pivot on the base 22, much like the accelerator of a car. A pair of side switches 28 projects outward from the base 22 on either side of the toe portion of the treadle 26. Electronic circuitry (not shown) within the foot pedal control 20 translates depression of the treadle 26 into a control signal for whatever surgical instrument (not shown) to which the foot pedal connects.

Figure 2:
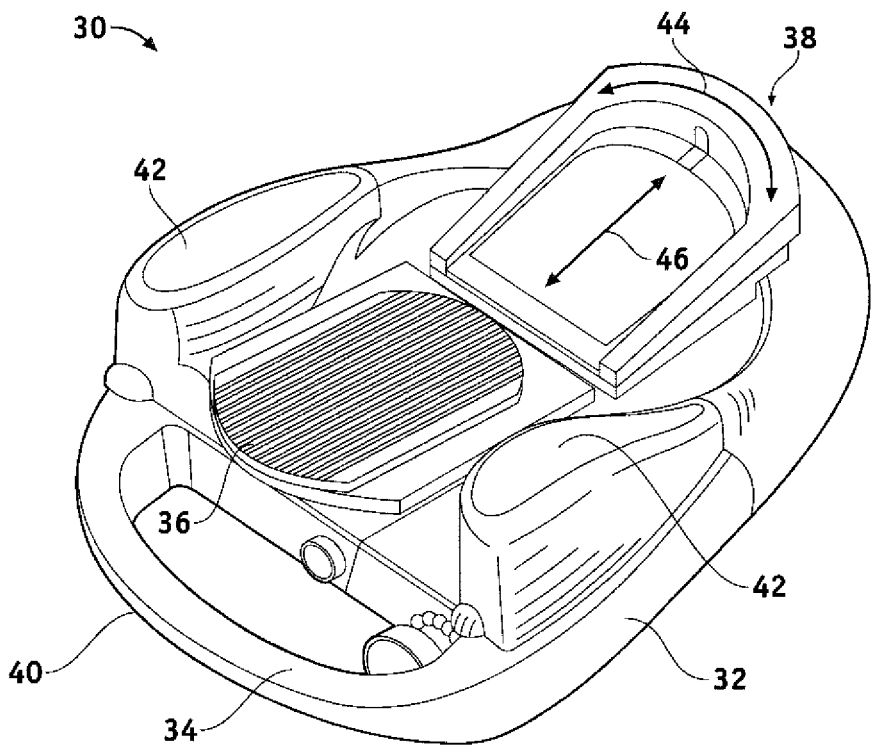
FIG. 2 is a perspective view of another prior art foot pedal control for ophthalmic surgery.

FIG. 2 shows another prior art foot pedal control 30 for ophthalmic surgery, as described in U.S. Patent Publication No. 2006/0219049 assigned to Alcon, Inc., of Fort Worth Tex. Alcon makes a similar looking foot pedal control and markets it in conjunction with its Infiniti® phacoemulsification surgical system. The foot pedal control 30 includes a body or housing having a bottom portion 32 and a top portion 34, and a foot pedal or treadle 36. The control 30 includes a separate heel cup assembly 38 and a carrying handle 40 positioned in the front. Side or wing switches 42 mount on the top housing portion 34 on either side of the treadle 36. It should be noted that the switches 42 mount to the housing and remain stationary until actuated by lateral contact with the user's foot from on the treadle 36.

The heel cup assembly 38 is positioned at the rear portion of the foot pedal control 30 to engage the heel of the operator, and allows the operator to rotate the heel cup assembly through an arcuate path 44. This movement produces an electrical signal received by encoder assembly (not shown) as an additional control signal to the surgical system. Furthermore, an ON/OFF switch is included in the heel cup assembly 38, such as a slide switch actuated by moving the heel cup assembly along a linear path 46. Although this design provides functionality, it is not the most intuitive or convenient to use.

Figure 3D:
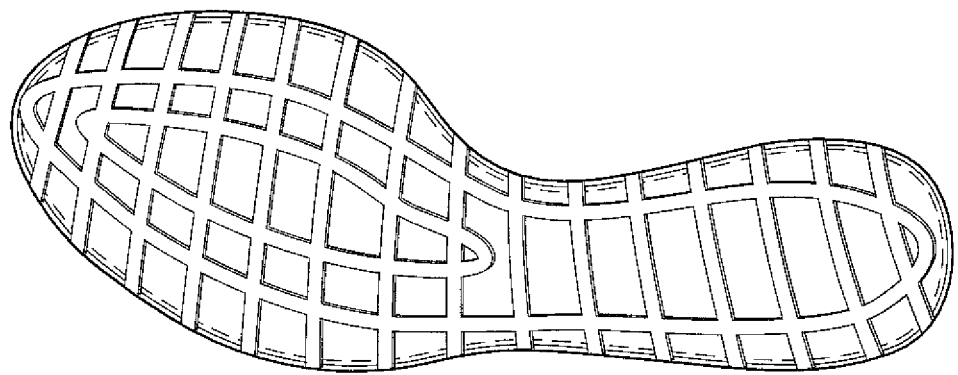
FIGS. 3A-3D are bottom plan views of a number of different shoe shapes.
Figure 3C:
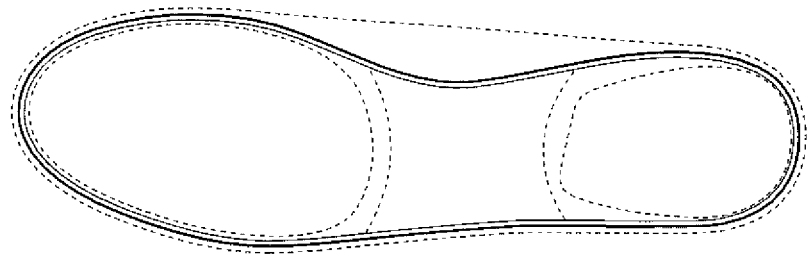
Figure 3B:
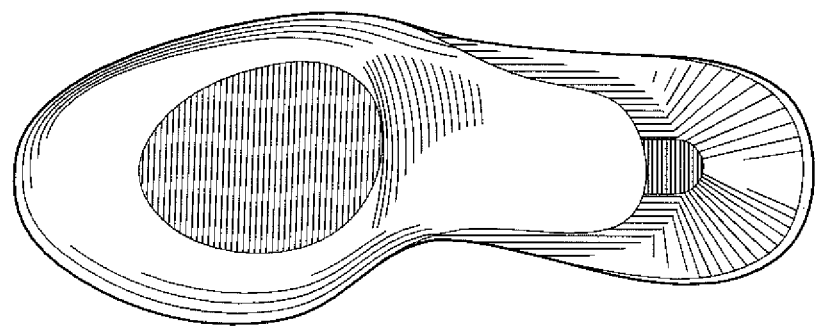
Figure 3A:
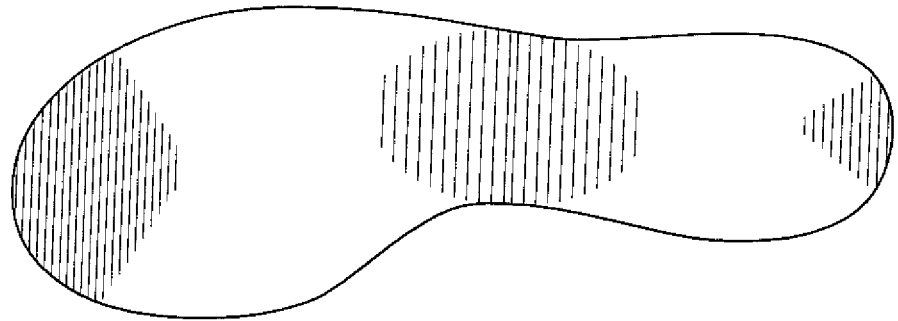

FIGS. 3A-3D are bottom plan views of a number of different shoe sole shapes to illustrate the wide variety of potential users of foot pedal controls. FIG. 3A is a standard flat sole preferred by many female medical professionals, in a relatively large shoe size for the left foot. FIG. 3B is a somewhat smaller-sized left-footed, high-heeled shoe with a larger metatarsal region. FIG. 3C shows an even smaller-sized low-heeled shoe for the right foot that is substantially narrower than the high-heeled shoe. Finally, in FIG. 3D the sole of a relatively large-sized running shoe for the right foot indicates a still further shape variation. Moreover, many medical professionals shed shoes in favor of socks or sterile booties, which add very little in the way of bulk and largely conform to the user's foot. Without belaboring the point, the reader will see that even in similarly-sized feet, the use of both right and left feet with different widths and shoe styles, or no shoes, creates thousands of permutations. Present foot control pedals provide relatively little adjustability, which often creates discomfort and at times impediments to proper operation of the pedal.

Figure 4:
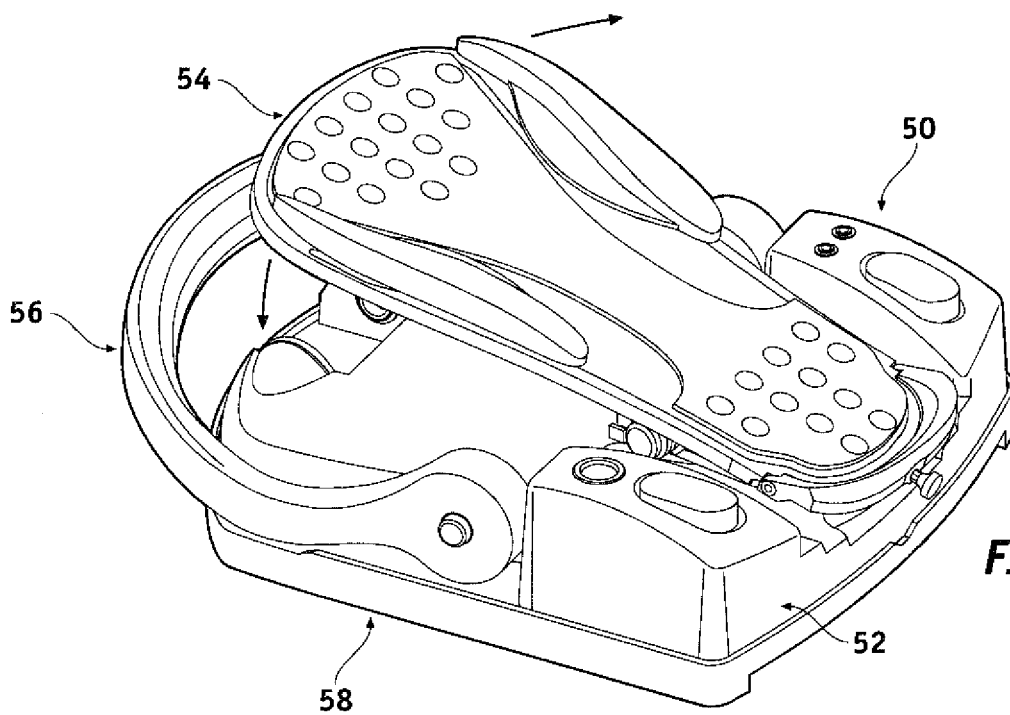
FIG. 4 is a perspective view of an exemplary foot pedal control for ophthalmic surgery described in the present application.

FIG. 4 is a perspective view of an exemplary foot pedal control 50 for use in a surgical system, for instance for ophthalmic surgery. The foot pedal control 50, as also seen exploded in FIGS. 6 and 7, comprises a base 52 on which is mounted a treadle 54 and a carrying handle 56. The base 52 has an undercarriage 58 arranged to lie flat on a ground surface. More specifically, the undercarriage 58 includes either a flat bottom surface or a series of separate feet that provide a stable base surface on the ground. For purpose of orientation, the foot pedal control 50 extends upward from the undercarriage 58, a forward or anterior direction is to the left in FIG. 4, and a rearward or posterior direction is to the right. Furthermore, in a preferred embodiment the treadle 54 is symmetric about a vertical medial plane bisecting the treadle into two substantially symmetric lateral (left and right) halves. The various components of the foot pedal control 50 may be made from any suitable material, such as stainless steel, titanium or plastic.

The treadle 54 mounts for movement on the base 52 to provide a movable control surface for the user. A variety of different movements for the treadle 54 may be provided, although the present invention provides particular advantages for treadles mounted for rotational yaw movement relative to the base 52, as seen by the movement arrows in FIG. 4. Alternatively, the treadle 54 may be mounted for pivoting movement in a vertical plane (pitch), as seen by the movement arrows in FIG. 5, or may be a dual-control treadle capable of both yaw and pivoting movement. The foot pedal control 50 further incorporates one or more sensors that track the movements thereof and generate an electronic signal therefor. As will be explained in the context of the surgical system shown in FIG. 19, the generated signal is used to control various functions of an operative tip, such as an ultrasonically vibrated needle with aspiration in a phacoemulsification/vitrectomy system.

Figure 5A:
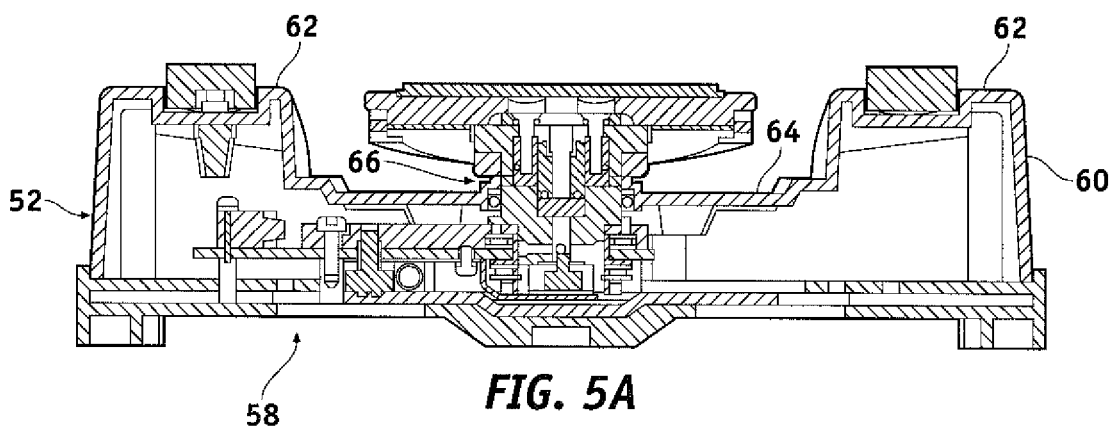
FIGS. 5 and 5A are side elevational and transverse sectional views of the foot pedal control of FIG. 4.
Figure 5:
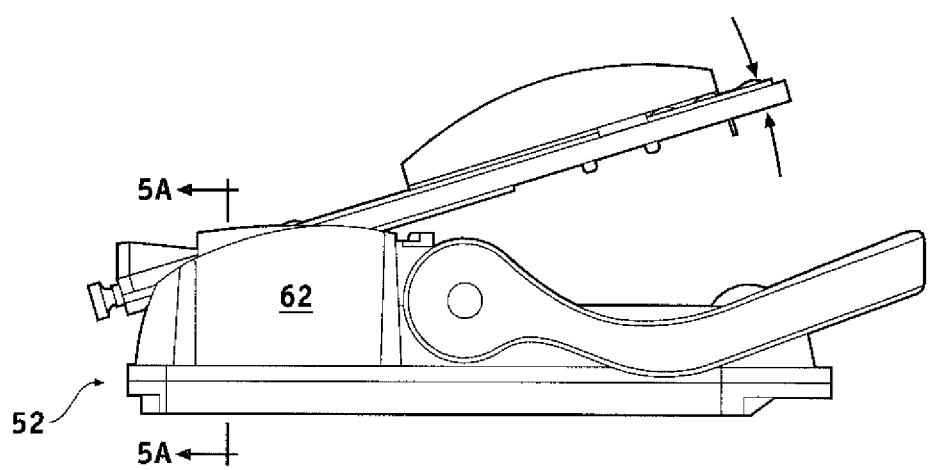

FIGS. 5 and 5A show the base 52 comprises a housing 60 having a pair of upstanding posterior shoulders 62 laterally flanking a central depression 64. A posterior end of the treadle 54 extends between the shoulders 62 and mounts on a dual-axis pivot assembly 66. As mentioned, the pivot assembly 66 enables both yaw movement and pitch (pivoting) movement in a vertical plane. That is, the anterior end of the treadle 54 may be moved side-to-side as indicated by the movement arrows in FIG. 4, or in a vertical plane as indicated by the movement arrows in FIG. 5. The pivot assembly 66 desirably incorporates biasing members (e.g., springs) that tend to return the treadle 54 to a neutral position having an angle to the vertical as seen in FIG. 5 and horizontally centered between the shoulders 62 and along a medial plane over the base 52. The treadle 54 range of movement is desirably symmetric about the medial plane so as to avoid any difference for left- and right-footed users.

Figure 7:
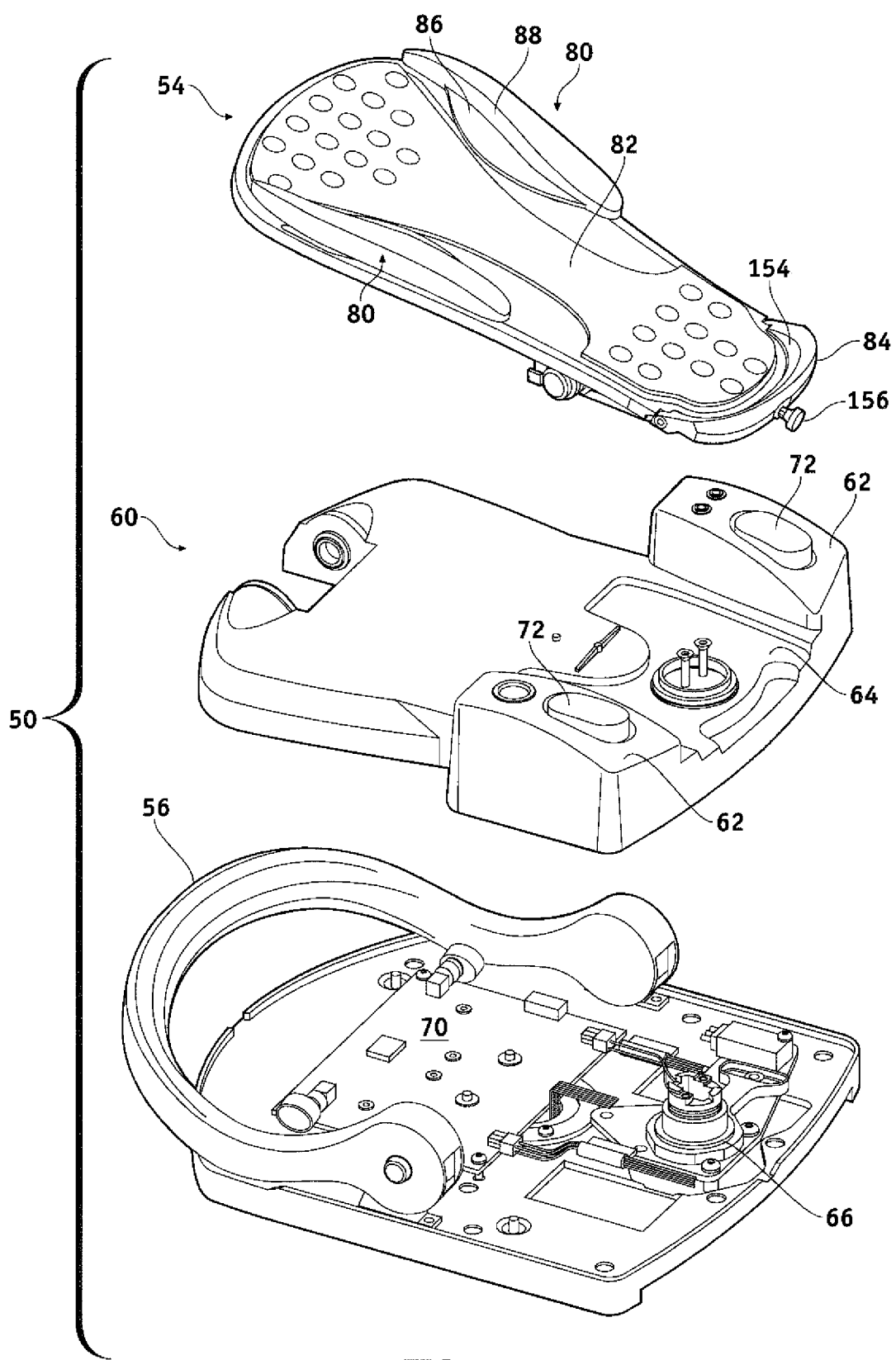
FIG. 7 is an exploded perspective view looking down on the foot pedal control of FIG. 4.
Figure 9A:
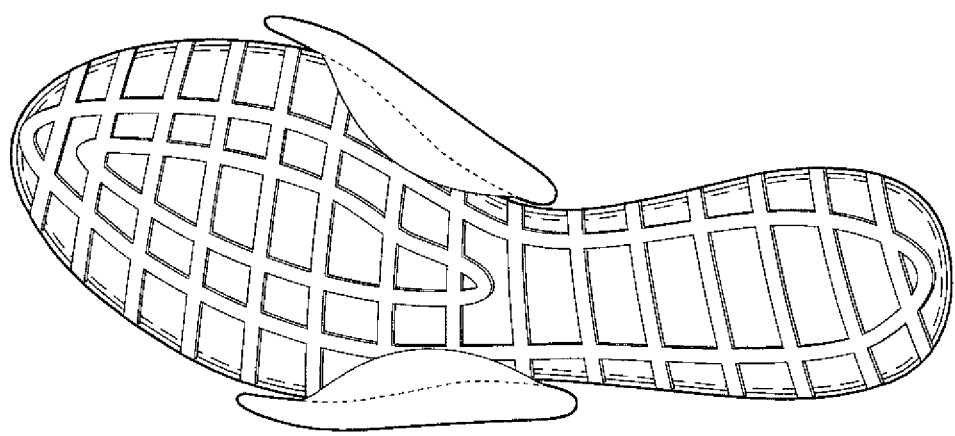
FIGS. 9A-9D are bottom plan views of different shoe shapes showing the adjustable guide rails conforming thereto.
Figure 9B:
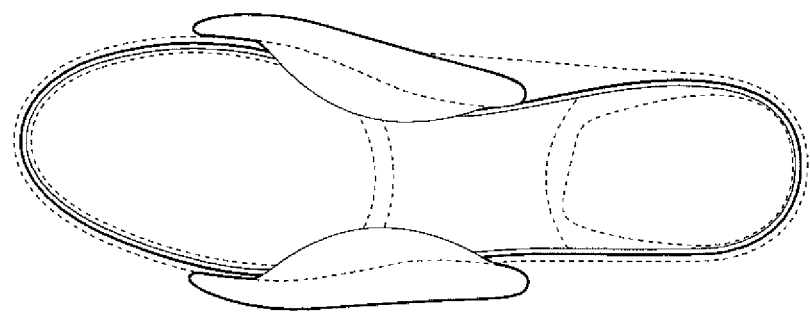
Figure 9C:
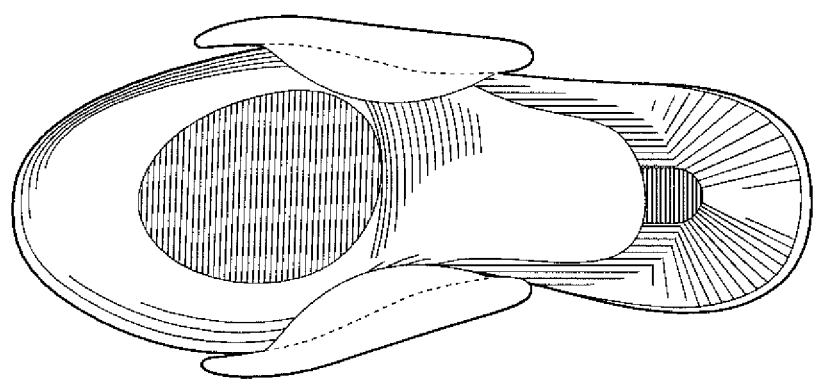
Figure 9D:
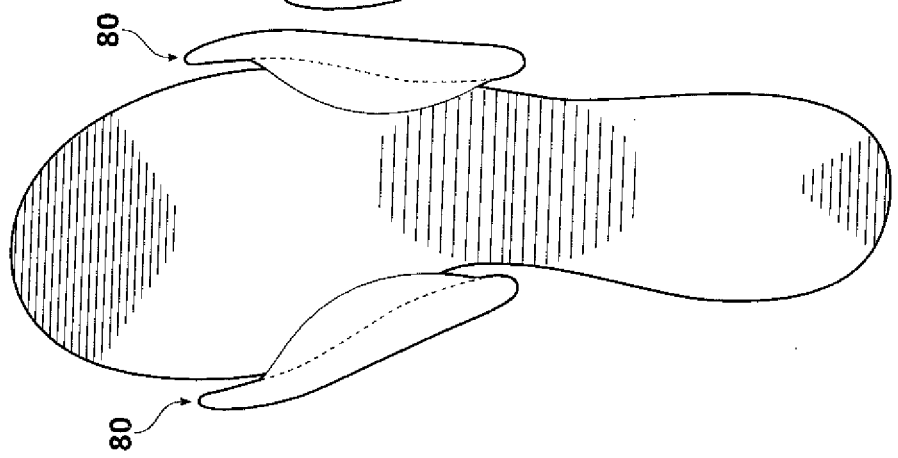

FIG. 7 best illustrates a circuit board 70 and various electronic components provided in the foot pedal control 50. The pivot assembly 66 registers with sensors, such as encoder assemblies, that translate the yaw position as well as the angular or pitch position of the treadle 54, and communicate with the circuit board 70. Also, separately functional side or wing switches 72 may be placed on the top of housing 60 on either side of the treadle 54, such as on the shoulders 62. The switches 72 provide alternative controls, such as power and operating mode controls. A wire or wireless transmitter (not shown) communicates the resultant signals to the aforementioned surgical system for controlling an operative tip thereof.

The foot pedal control 50 of the present invention incorporates a number of features that greatly improved the ease-of-use thereof for a variety of different foot and/or shoe sizes and styles. With reference to FIG. 7, among others, a pair of laterally-adjustable guides 80 mount on the treadle 54 flanking a central foot platform 82. In a preferred embodiment, the foot platform 82 has a non-slip (e.g., rubber) liner with bumps or other friction-enhancing features. Also, a heel stop 84 may be converted between an up position as shown for receiving and supporting the heel of the user, and a down position out of the way of the user. Additionally, the carrying handle 56 converts between at least two positions depending on the preference of the user, as will be explained below. Finally, various ergonomic shapes, surfaces, and placements of the functional features of the foot pedal control 50 facilitate use by a variety of foot sizes and shapes. It should be understood that each of these advantages may be incorporated into existing foot pedal controls by themselves, or in combination with any of the others.

First with reference to FIGS. 8A and 8B, the adjustable guides 80 are shown in two different potential positions on the treadle 54. In these views, up on the page corresponds to the anterior direction, down corresponds to the posterior direction, a medial plane M extends out of the page through a central plane of the treadle 54, and the adjustable guides 80 are disposed laterally outward therefrom, flanking the foot platform 82. In FIG. 8A, the guides 80 are shown displaced laterally outward from the medial plane M, and upward in an anterior direction, while in FIG. 8B the guides or displaced laterally inward toward the medial plane M and downward in a posterior direction. In the illustrated embodiment, the adjustable guides 80 are mounted to the treadle 54 and move between these two positions in tandem. However, as will be explained below, various other possible configurations for the guides 80 are contemplated.

The lateral inward and outward movement of the guides 80 relative to the medial plane M adjusts the spacing therebetween. This provides flexibility for users having different sizes of feet or shoes, as the case may be. As mentioned above, many users operate foot controls wearing just socks, while others prefer to leave their shoes on. Preferably, the guides 80 adjust inward to a minimum spacing to accommodate the smallest user foot without a shoe, such as women's' size 5, while they also adjust outward to a maximum spacing to accommodate large shoes such as size 13 men's'.

FIGS. 9A-9D illustrate the same shoe bottoms as previously described with respect to FIGS. 3A-3D, but this time showing the adjustable guides 80 on either side thereof in different locations conforming to the various shoes. It should be noted that the guides 80 are shown not only moved laterally inward or outward, and upward or downward (anterior or posterior), but also rotated to conform to the various shoes. Although the illustrated mechanism for displacing the guides 80 does not explicitly accommodate such rotation, it is shown here to illustrate a further possible movement. The guides 80 may be adjusted to contact either side of the shoes, or merely be relocated to reduce the space between the shoes and the guides.

With reference again to FIGS. 7 and 8A-8B, each of the guides 80 is elongated in an anterior-posterior direction and includes a lip 86 extending toward the other guide and generally parallel to the foot platform 82. Each guide 80 further includes a rail 88 extending upward from the lip 86 and generally perpendicular to the foot platform 82.

The shallow lips 86 provide sock-catchers, in a manner of speaking, in that they help prevent the guides 80 from snagging loose booties or socks during adjustment or movement of the foot. The lips 86 are generally tapered downward in height toward the medial plane M from the rails 88, and the user at all times steps on the lips which helps prevent folds of the sock from getting trapped under the guides. The lips 86 are also rounded to eliminate any corners to catch on socks.

The anterior-posterior length of the upstanding rails 88 desirably provides enough surface area for the user to comfortably laterally press his or her foot on either guide and cause the treadle 54 to rotate in the yaw direction. That is, although the rails 88 may be as small as a post and still provide a reaction surface against which to engage the foot, they desirably have a length of at least 38 mm (1.5 inches) for comfort and greater control.

Additionally, the height of the rails 88 is desirably great enough to prevent the user's sock-covered foot or shoe from riding over them, but is not too great to permit the user to easily lift his or her foot out from between the guides when needed. For example, the user may wish to regularly actuate one or both of the two wing switches 72, which require rapidly placing and removing the foot between the guides 80. In a preferred embodiment, the guides 80 have an upward height generally perpendicular to the foot platform 82 of between about 15 mm (0.6 inches) and 38 mm (1.5 inches).

The guides 80 are desirably contoured to match typical foot shapes. As mentioned, the user may be wearing a sock or some type of shoe, but all feet and shoes are somewhat narrow toward the arch and heel, or on a posterior end, and broader adjacent the metatarsal bones, or on the anterior, forward end. Therefore, the exemplary guides 80 are slightly outwardly angled in an anterior direction, as indicated in FIG. 8A, by the angle θ between a line extending from one tip to another of the guide and a reference line parallel to the medial plane M. Furthermore, the guides 80 desirably have an S-shaped so as to define both convex and concave regions on their inner faces that conform to different areas of users' feet. More particularly, a convex-inward posterior segment 90 and a concave-inward anterior segment 92 match concave arch and convex metatarsal areas, respectively, of typical foot/shoe shapes. Finally, as seen best in FIG. 7, the axial height of the rails 88 varies from a maximum at the midpoint to reduce heights at the anterior and posterior tips. That is, the rails 88 are gradually tapered to have a taller middle and shorter ends. This helps avoid snagging socks on the rails, and also facilitates moving the foot in out from between the rails. Furthermore, the tapered height reduces corner angles in case the user accidentally steps down hard on them.

As mentioned above, the exemplary guides 80 desirably translate along angled slots in the treadle 54, and are mounted so as not to rotate. However, other alternatives are possible. For example, one of the guides 80 may be stationary while the other adjusts. A simple alternative adjustable guide comprises blocks having pins that are movable between a series of holes in the treadle 54. For example, both guides 80 shown in FIG. 8A may be completely separated from the treadle 54 and replaced in different holes to create the spacing shown in FIG. 8B. The matching pins and holes for such separate blocks desirably prevent rotation of the guides for stability. For instance, the matching pins and holes may be other than circular, or more than one matching pin and hole combination for each guide may be provided.

Figure 10:
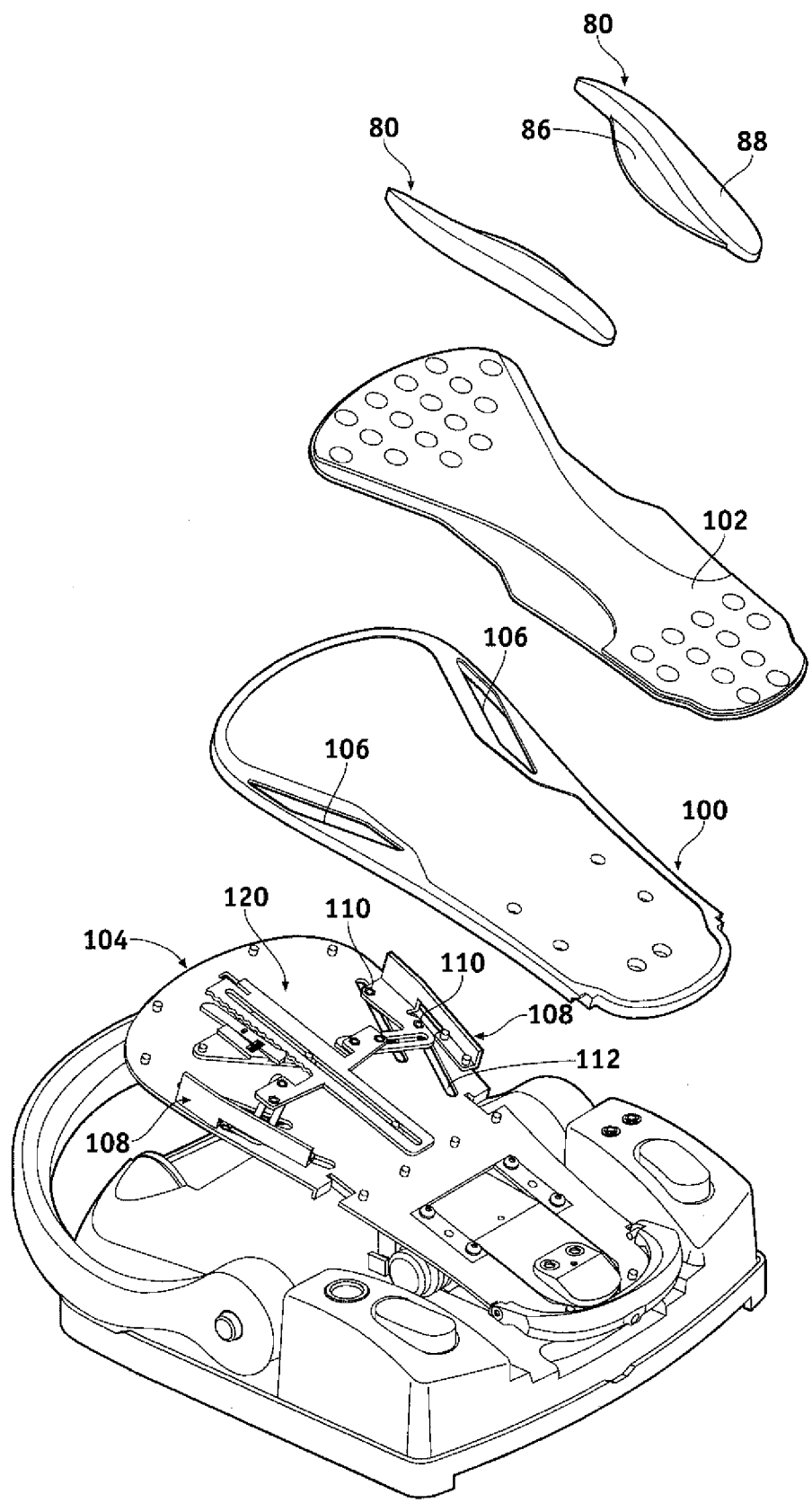
FIG. 10 is an exploded perspective view of the treadle of the foot pedal control of FIG. 4.
Figure 11:
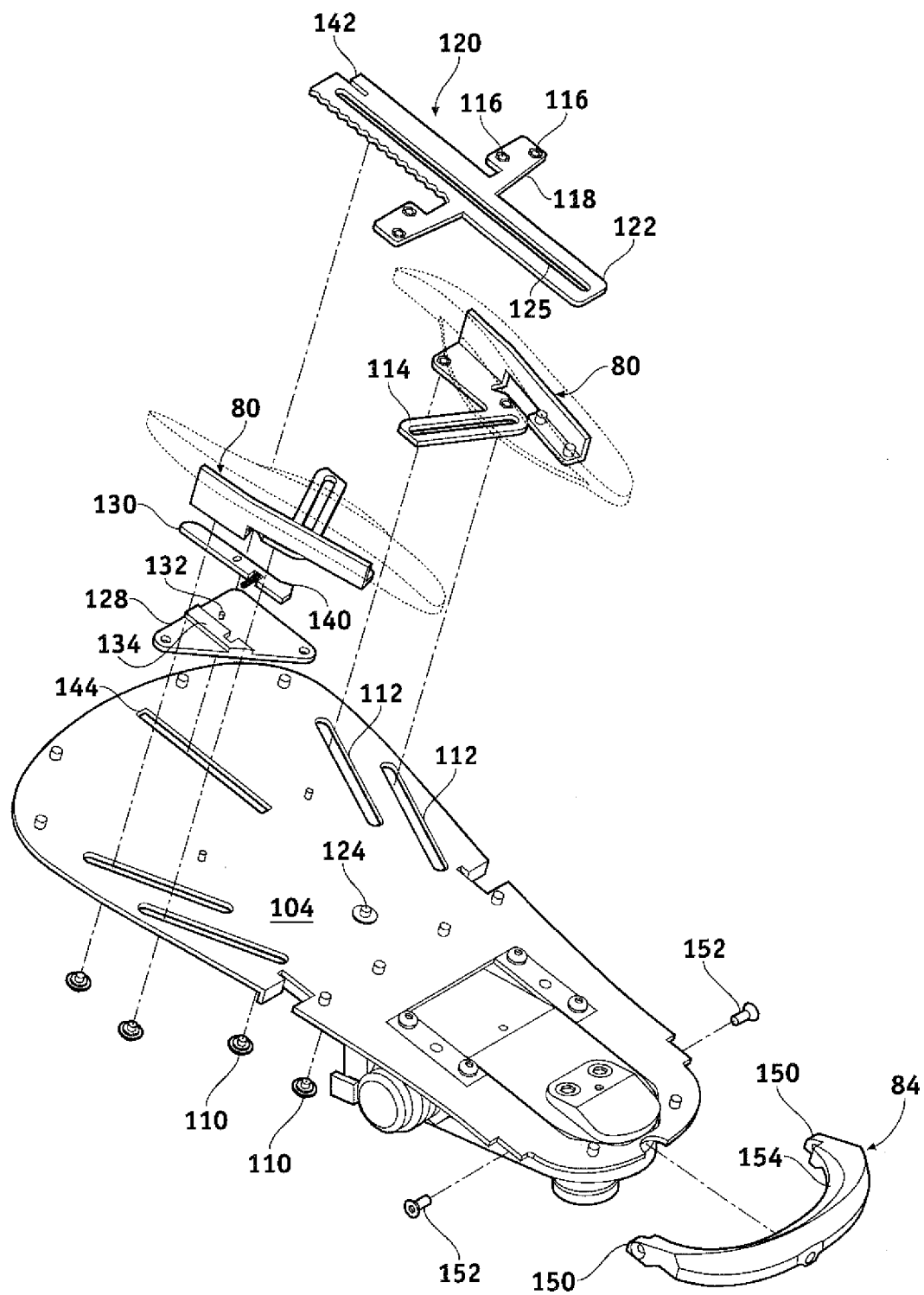
FIG. 11 is an exploded perspective view of an actuation plate of the treadle of FIG. 8.

FIGS. 10 and 11 are exploded perspective views of the treadle 54 of the foot pedal control 50 showing an exemplary lateral adjustment mechanism. The treadle 54 includes a foot plate 100 on which a rubber cover 102 is placed to define the central foot platform 82. The foot plate 100 mounts to and covers a lower actuation plate 104. The foot plate 100 further includes a pair of angled slots 106 through which upstanding brackets 108 from the foot plate extend. The brackets 108 fit within similarly-shaped receptacles on the underside of each of the guides 80 (FIG. 11).

Figure 6:
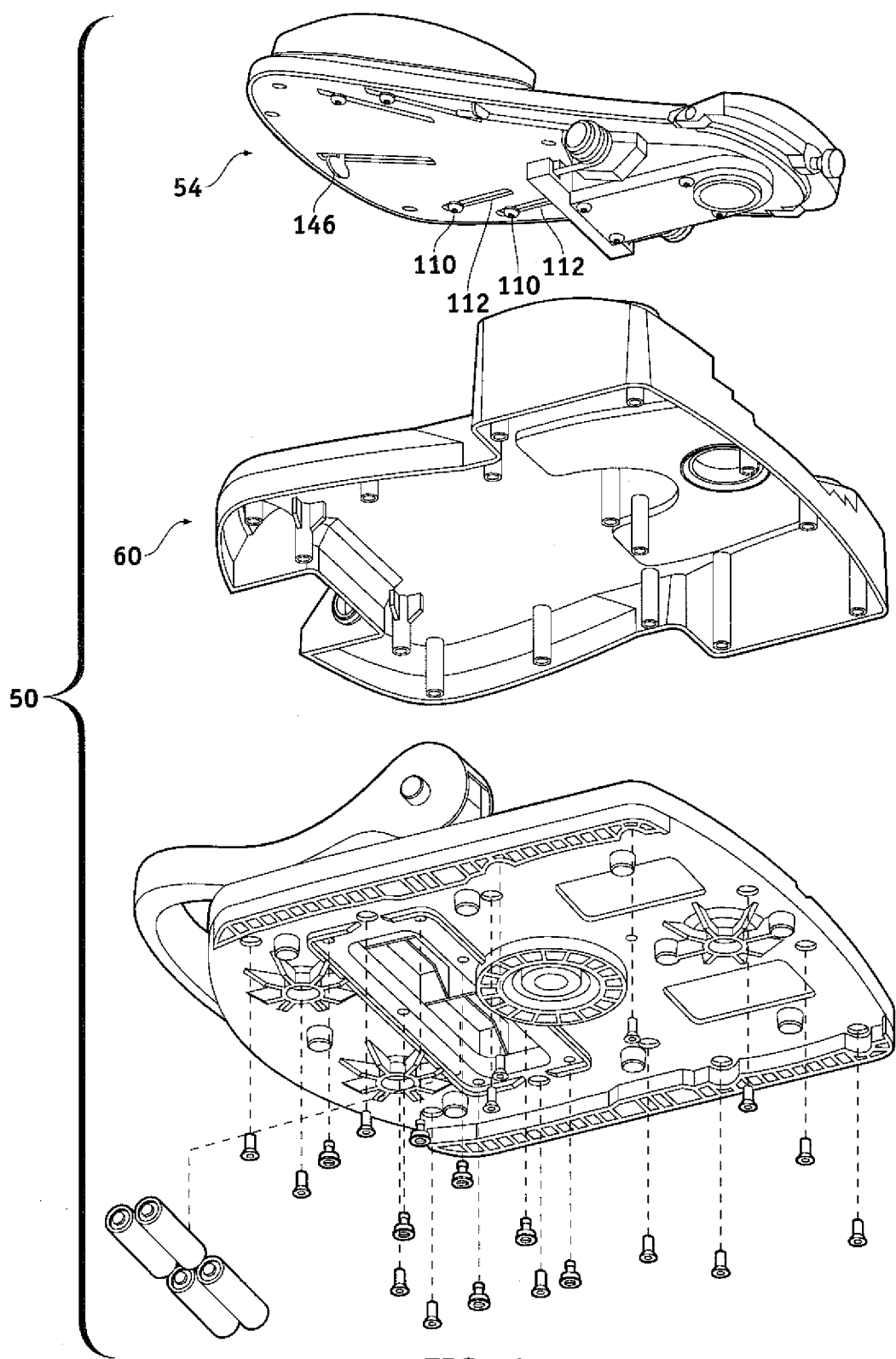
FIG. 6 is an exploded perspective view looking up on the foot pedal control of FIG. 4.

As seen exploded in FIG. 11, the brackets 108 each receive two guide pins 110 (e.g., rivets) that slide along a pair of parallel guide slots 112 provided in the actuation plate 104 (seen from below in FIG. 6). The brackets 108 each feature an inwardly angled finger 114 having a slot therein that receives a pair of pins 116 on one of two oppositely extending wings 118 of a central ratchet member 120. The ratchet member 120 is in the shape of a cross with an elongated central beam 122 and the outwardly extending wings 118. Upstanding pegs 124 in the actuation plate 104 project through a central channel 125 in the ratchet member 120. One of the upstanding pegs 124, along with a secondary peg 126 (see FIG. 12B), secures a triangular plate 128 to the foot plate 100. A pawl member 130 is mounted to rotate about a pin 132 on the plate 128. As seen best in FIGS. 12A and 12B, the pawl member 130 is constrained for minimal lateral movement between an upstanding step 134 on the plate 128 and a series of ratchet teeth 136 on the ratchet member 120. A small spring the biases a pawl 140 on the pawl member 130 toward the ratchet teeth 136.

Now with reference to FIGS. 10 and 12A-12B, which show the assembled actuation plate 104, the movement of the various linked parts will be described. The ratchet member 120 overlays both the triangular plate 128 and the inwardly angled fingers 114 on each of the brackets 108. The ratchet member 120 further includes a bent tab 142 that protects downward into an elongated channel 144 in the actuation plate 104 (see also FIG. 11). The upstanding pegs 124 and cooperation between the bent tab 142 and channel 144 constrain the ratchet member 120 to longitudinal movement over the actuation plate 104. The two pins 116 on each of the oppositely extending wings 118 of the ratchet member 120 therefore remain in the same relative orientation and translate longitudinally. Interaction between the pins 116 and the slots in the angled fingers 114 of the brackets 108 links movement of the ratchet member 120 to movement of the brackets. At the same time, the cooperating pins 110 restrict movement of the brackets 108 to linear movement along the angled slots 112 in the actuation plate 104. The brackets 108 can move laterally with respect to the ratchet member 120 by virtue of the sliding play between the pins 116 and the slots in the angled fingers 114.

FIGS. 12A and 12B show two different positions of the mechanism. In FIG. 12A the central ratchet member 120 is relatively high on the actuation plate 104 as seen by the relative positions of the lower peg 124 in the bottom of the longitudinal channel 125. The pins 116 on the outwardly extending wings 118 are close to the innermost end of the slots in the angled fingers 114 of the brackets 108. At the same time, the pins 110 on the brackets 108 are close to the top ends of the angled slots 112 in the actuation plate 104. This corresponds to the position of the guides 80 shown in FIG. 8A.

In FIG. 12B the brackets 108 as well as the ratchet member 120 have been displaced downward, corresponding to the position of the guides 80 shown in FIG. 8B. The simultaneous change in position of the various pins and slots are evident and will not be further explained. It should be noted, however, that a number of the ratchet teeth 136 have descended past the spring-biased pawl member 130. This corresponds to a series of stop positions for the ratchet member 120 distinguished by audible and/or tactile clicks. Although not required for lateral guide adjustment, such a ratcheting configuration helps the operator quickly adjust the guides 80 to the desired position.

It should also be noted that a movement of the guides 80 may be accomplished by either manually displacing one or both of the guides 80 from the top of the treadle 54, or by linearly displacing the bent tab 142 that extends through the channel 144 to the underside of the treadle. Of course, a more ergonomically comfortable (plastic) knob or lever may be mounted on the end of the bent tab 142, such as the widened grip 146 seen in FIG. 6. The angle at which the guides 80 move along slots in the treadle 54 should be selected so that the guides can be easily moved by hand yet hold their lateral positions against foot movement. More specifically, as seen in FIG. 12B, the angled parallel guide slots 112 along which the brackets 108 slide may extend from a posterior point outward in an anterior direction at an angle $\alpha$ of between about 15° and 45° from a longitudinal axis of the treadle 54, preferably between about 15° and 30°, and in an exemplary embodiment a is about 25°. Note that from FIGS. 8A and 8B the longitudinal axis of the treadle 54 corresponds to the medial plane M bisecting the treadle into two substantially symmetric lateral halves. The slots 106 in the foot plate 100 also mirror this angle, though some play may be introduced to accommodate the shape and/or rotation of the brackets 108.

It should be noted that other means for displacing the guides 80 are contemplated other than those described and illustrated. In a simple version the guides 80 slide along the same angled slots but without the connecting/ratcheting structure. The guides may be locked in place with a bolt/wing nut combination accessed under the treadle 54. Or, the guides may be arranged to pivot about axes perpendicular to the foot platform 82, and locked in position with a threaded tightener. In another example, the guides 80 may be spring-biased into their outward-most position and automatically constrict to conform to the user's foot after the user steps on the foot platform 82. When the user removes his or her foot, the guides 80 spring outward again to be ready to accommodate the largest feet/shoe. Another possible means for translating the guides 80 is a motor of some sort. Much like the adjustment of a car seat, the user may have full control over an infinite number of positions of the guides 80, in tandem or separately, using electronic control switches.

Figure 13A:
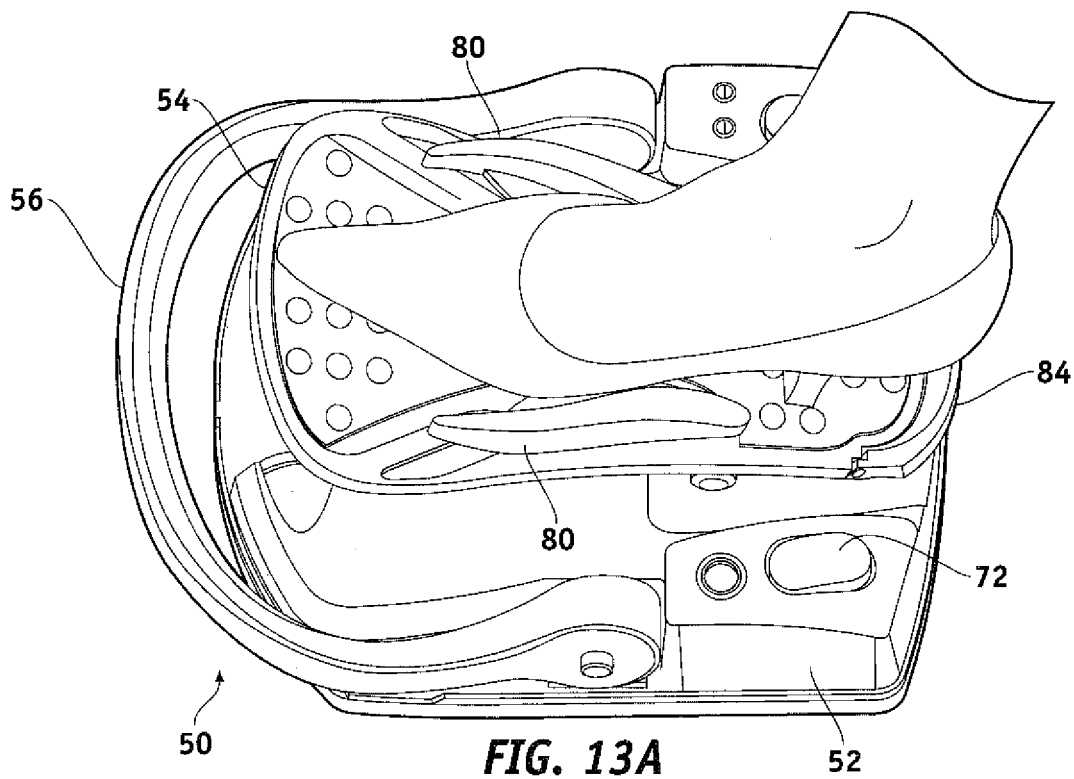
FIGS. 13A and 13B are perspective views of the foot pedal control of FIG. 4 showing adjustment to fit two different sizes and shapes of shoes.
Figure 13B:
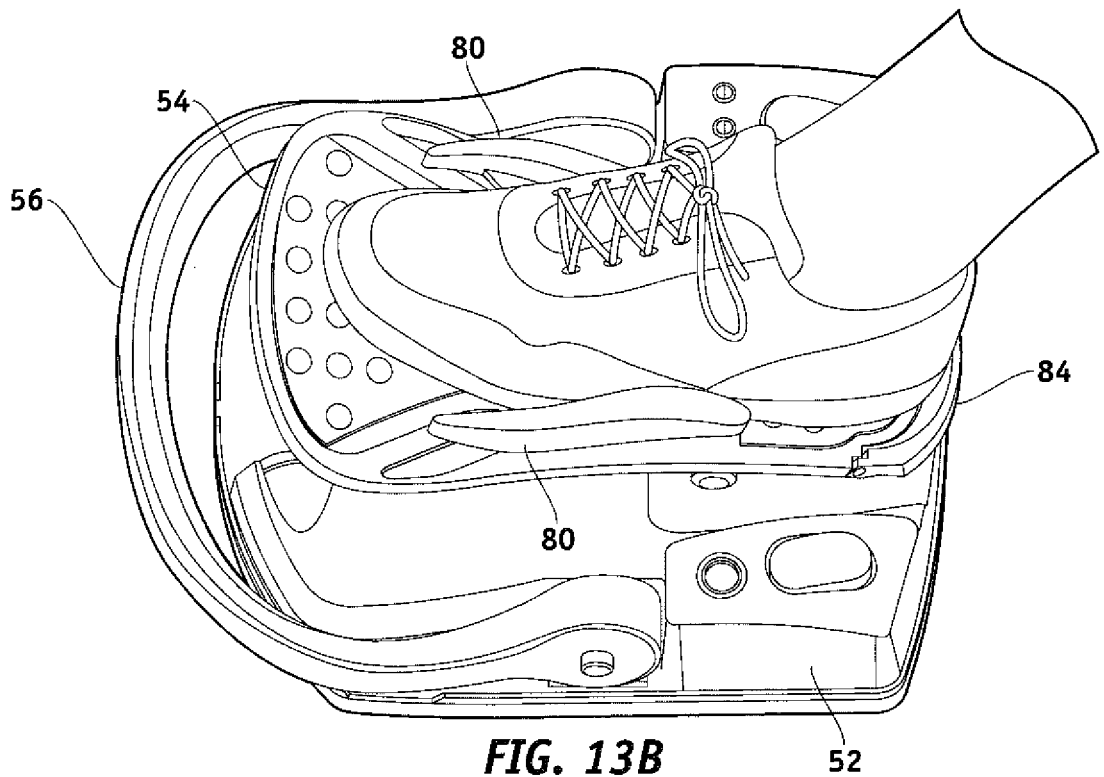

FIGS. 13A and 13B are perspective views of the foot pedal control 50 showing the guides 80 adjusted to fit two different sizes and shapes of shoes. Specifically, FIG. 13A illustrates the guides 80 adjusted to fit a relatively narrow woman's heeled shoe, while FIG. 13B shows the guides conforming around a flat-soled somewhat broader shoe. The reader will also note that the carrying handle 56 lies out of the way and generally parallel to the ground, or in terms of the foot control pedal, parallel to the undercarriage of the base 52. This permits the user to easily engage and disengage the foot pedal control 50, and also to actuate the wing switches 72.

Furthermore, FIG. 13A shows the heel stop 84 in its down position which may be preferred for the high-heeled type of shoe shown. That is, this type of shoe does not conform easily to the heel stop 84, and thus the heel stop is most likely pivoted down out-of-the-way. In contrast, the shoe in FIG. 13B conforms nicely to the concave heel stop 84, which is in the up position.

With reference back to FIGS. 7 and 11, the exemplary heel stop 84 comprises an arcuate rigid member having two free ends 150 with through holes that pivot on a common axis about pins 152 secured at the rear sides of the actuation plate 104 of the treadle 54. The concave inside curvature of the heel stop 84 closely conforms to the convex posterior end of the treadle 54. An inside chamfer 154 on the upper corner of the heel stop 84 facilitates release of the user's foot from the treadle 54, especially in cases where the posterior end of the user's shoe sole is highly angled. A small locking button 156 may be mounted through a midline of the heel stop 84 for engagement with a depression or other such feature on the posterior end of the treadle 54. The locking button 156 is desirably spring-loaded toward the treadle 54, whereby the user simply pulls a button in a rearward direction to release and pivot the heel stop 84 between its up and down positions. The locking button 156 automatically clicks back into one of its locking positions. It should be noted here that the heel stop 84 may alternatively be provided as a member separable from the treadle 54 which can be stored on the base 52, for example, until needed, and then simply inserted into mounting holes in the treadle.

Figure 14A:
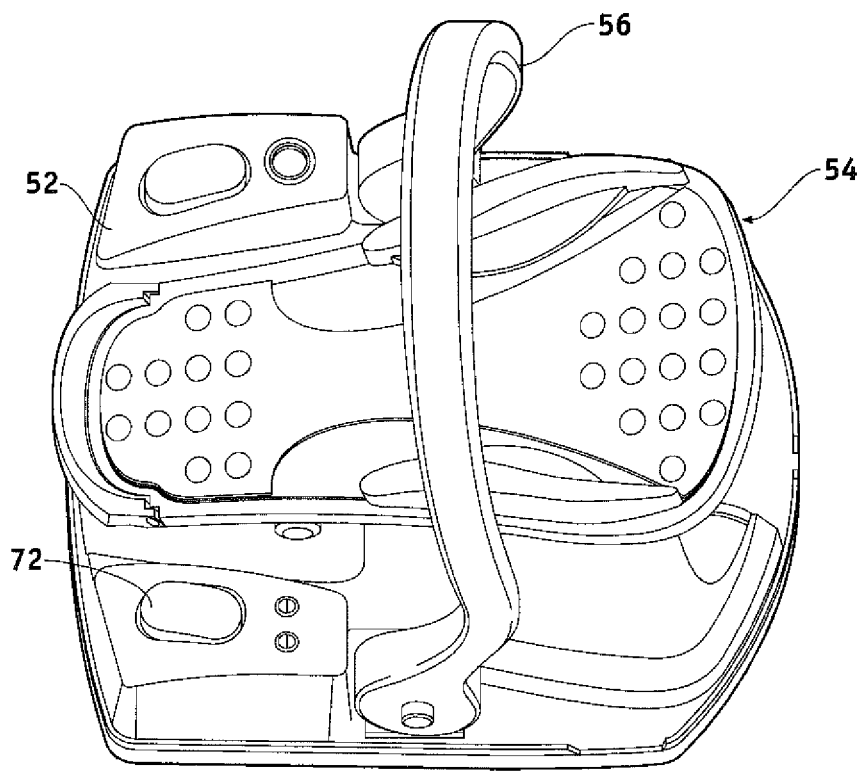
FIGS. 14A and 14B are perspective views of the foot pedal control of FIG. 4 showing two different positions of a carrying handle.
Figure 14B:
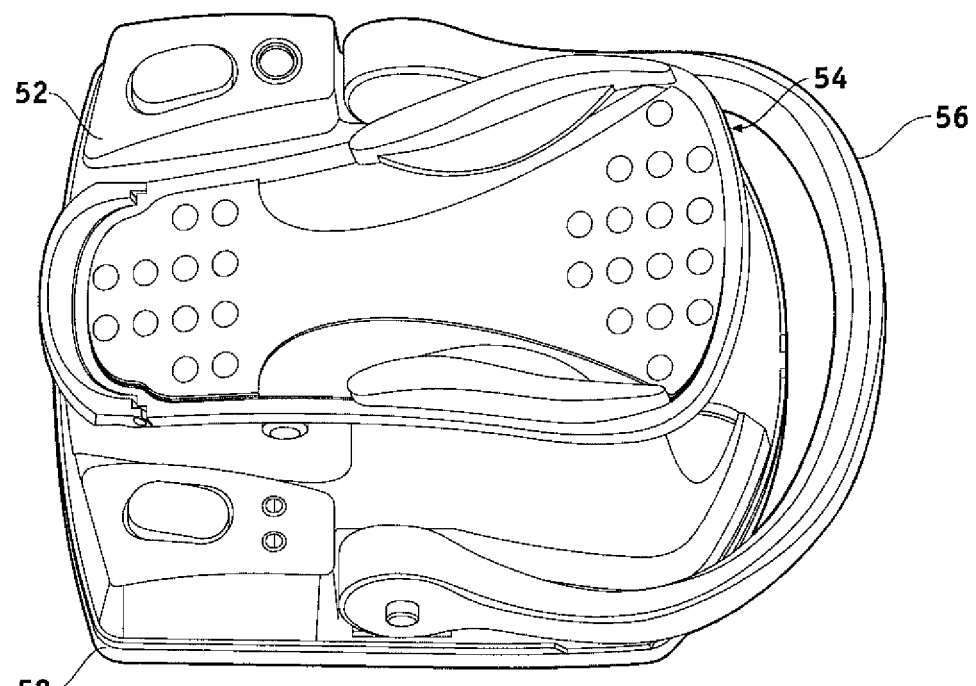

FIGS. 14A and 14B show the two different positions of the carrying handle 56, which connects to the base 52 and converts between at least these positions—a first position above the treadle 54 and generally perpendicular to the undercarriage 58 of the base (FIG. 14A), and a second position out of the way of the treadle 54 and generally parallel to the undercarriage 58 (FIG. 14B). As mentioned above, the second position may be preferred by those users who like easy entry and removal of their foot from the foot pedal control 50, especially if the procedure requires constant use of the wings switches 72. On the other hand, some users may prefer the first position with the carrying handle 56 over the treadle 54 to provide a measure of protection from others inadvertently stepping on the control surfaces, or as a means to easily reposition the foot pedal control 50 during a surgical procedure.

Figure 15:
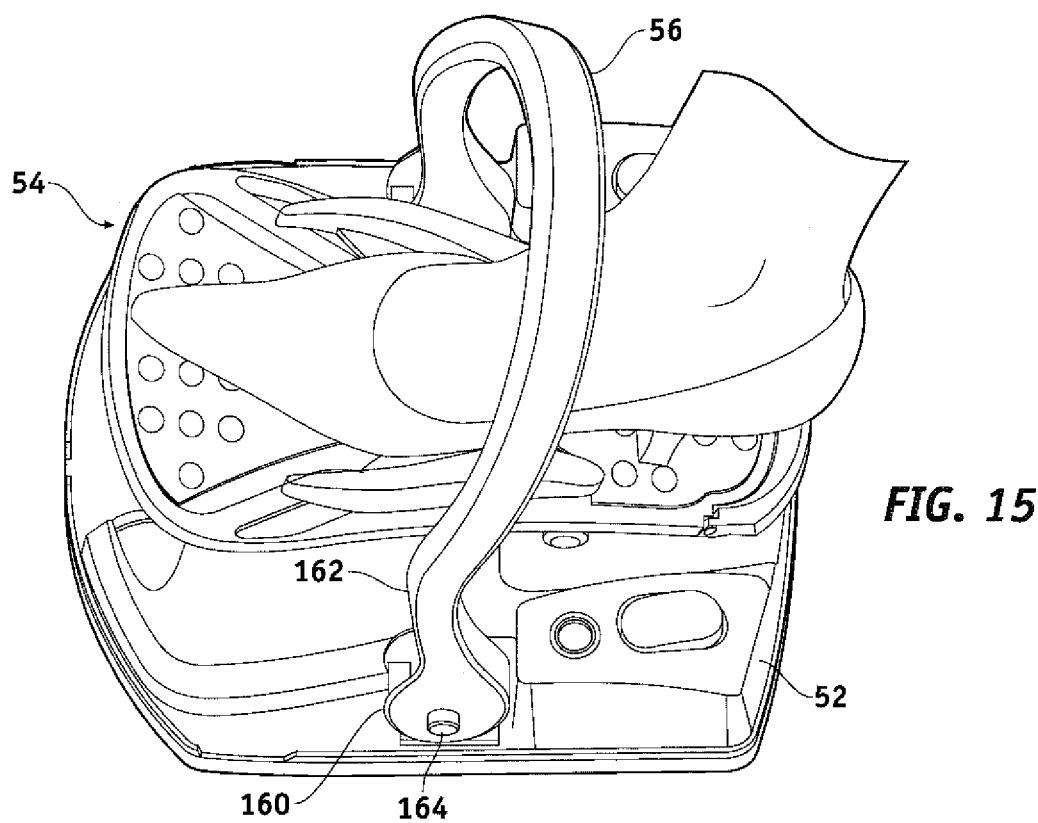
FIGS. 15 and 16 are perspective views of the foot pedal control of FIG. 4 with the carrying handle in a raised position to illustrate different benefits during use.
Figure 16:
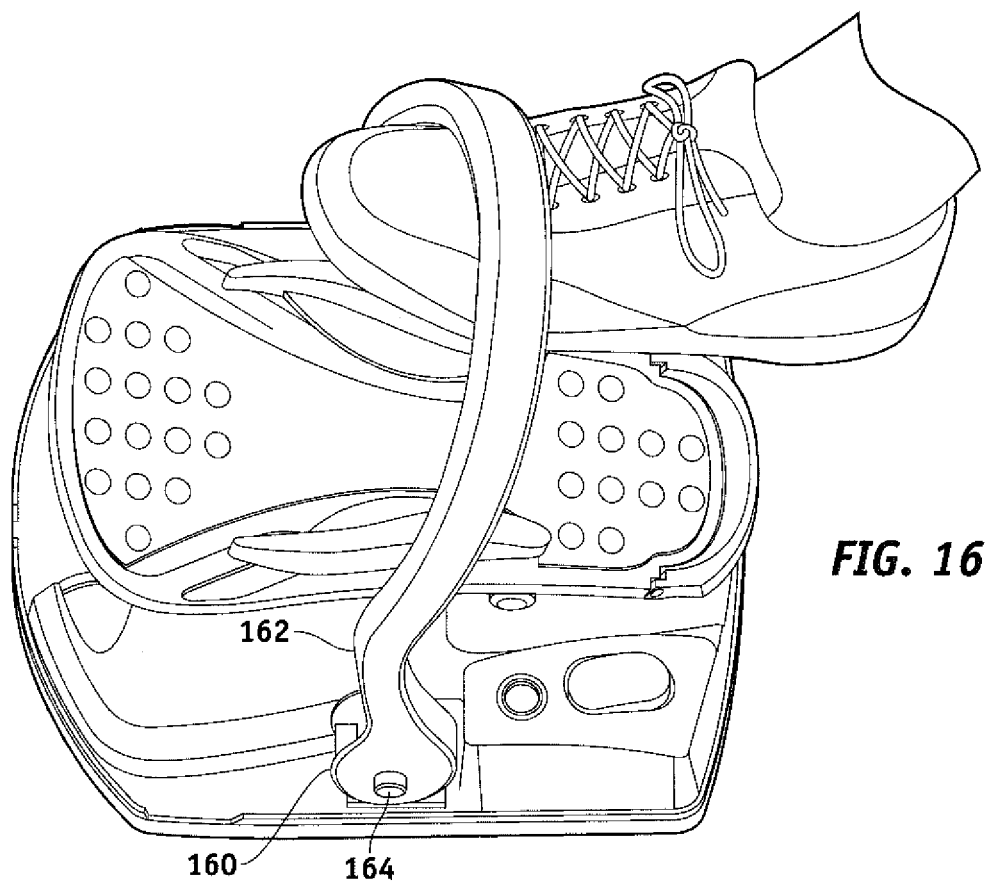

FIGS. 15 and 16 show two different users' feet in the foot pedal control 50 with the carrying handle 56 in its first position above the treadle 54. Even with the carrying handle 56 up, as in FIG. 15, the user can easily access the wings switches 72 because of the contours of the handle. More specifically, the carrying handle 56 preferably defines an inverted U-shape with two free ends 160 that mount to the base 52 and pivot about a common axis parallel but offset with respect to a plane defined by the undercarriage 58 of the base. Curvilinear side struts 162 are shaped to be convex in the anterior direction to arc out of the way of side movement of the user's foot. That is, a relief area provided by the arcuate side struts 162 facilitates sideways movement of the user's foot when attempting to actuate the wings switches 72 or otherwise remove the foot from the treadle 54. FIG. 16 illustrates another use of the carrying handle 56 when it is in its first or up position. Namely, the user can reposition the entire foot pedal control 50 by lifting it with his or her foot on the underside of the carrying handle 56. The convertible carrying handle 56 thus provides enhanced flexibility for the foot pedal control 50.

Although two primary positions of carrying handle 56 are shown, it may be adapted to be secured in other positions. In a preferred embodiment, one or more locking detents secure the carrying handle 56 in various discrete positions. For example, the illustrated embodiment shows a lock/release button 164 extending outward from each of the free ends 160 of the carrying handle 56. Desirably, the user depresses both of the buttons 164 inward against a spring bias to release the carrying handle 56 for conversion between various positions. Although not shown, those of skill in the art will understand that various depressions or grooves may be provided on the side of the base 52 with which inner ends of the buttons 164 register at the discrete stop positions. Although only one button 164 is needed to lock the carrying handle 56, two buttons requires both hands to operate and may help prevent inadvertently trapping a finger or other appendage between the pivoting handle 56 and the base 52.

Figure 17A:
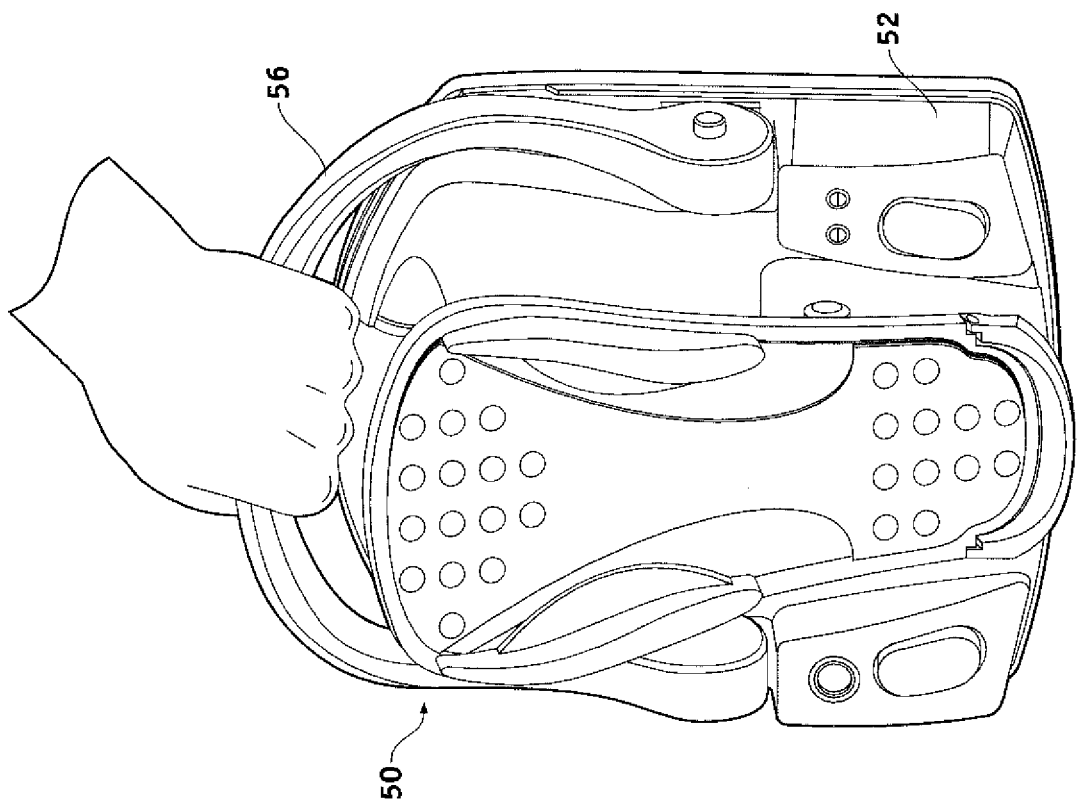
FIGS. 17A and 17B illustrate two different methods of carrying the foot pedal control of FIG. 4 with the handle in raised and lowered positions, respectively.
Figure 17B:
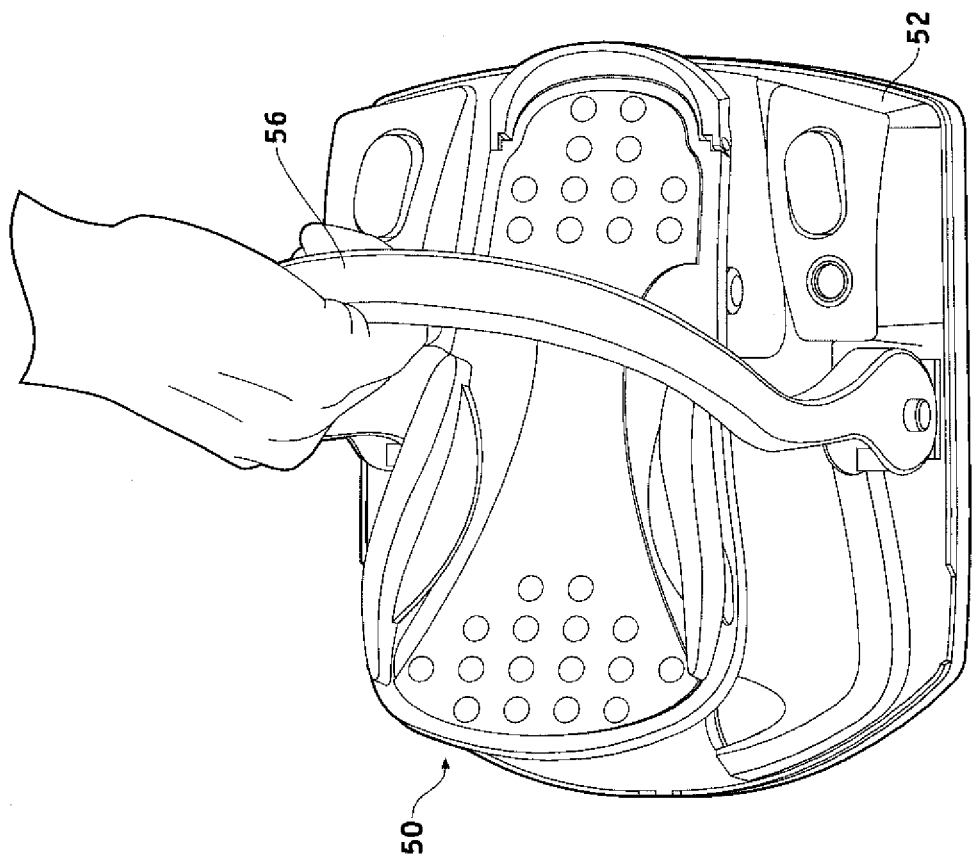

FIGS. 17A and 17B show two different methods of carrying the foot pedal control 50 with the carrying handle 56 in raised and lowered positions, respectively. As mentioned previously, with the carrying handle 56 in its raised position the foot pedal control 50 may be repositioned short distances with the user's foot. However, the entire unit may be easily lifted and move to a different area in the operating room with the handle 56 in the up position of FIG. 17B, especially if it is a wireless unit. Alternatively, a user can carry the foot pedal control 50 with the handle 56 converted to lie parallel to the undercarriage of the base 52, as in FIG. 17A, which results in a lower overall profile, typical for storage. One version of the foot pedal control 50 weighs between 10-11 lbs.

Figure 18A:
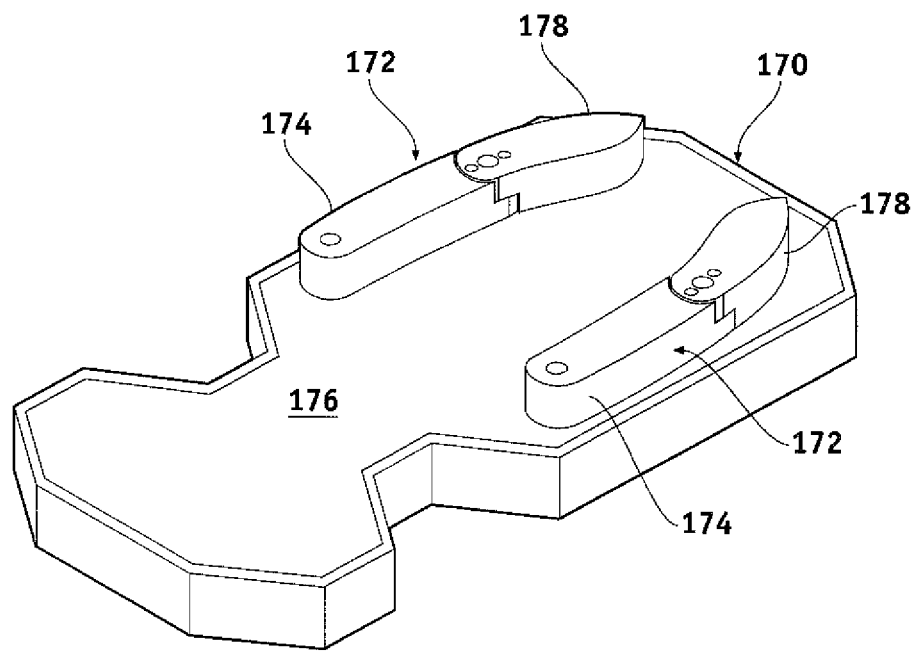
FIGS. 18A and 18B are two perspective views of an alternative foot pedal control treadle having articulated laterally-adjustable guides.
Figure 18B:
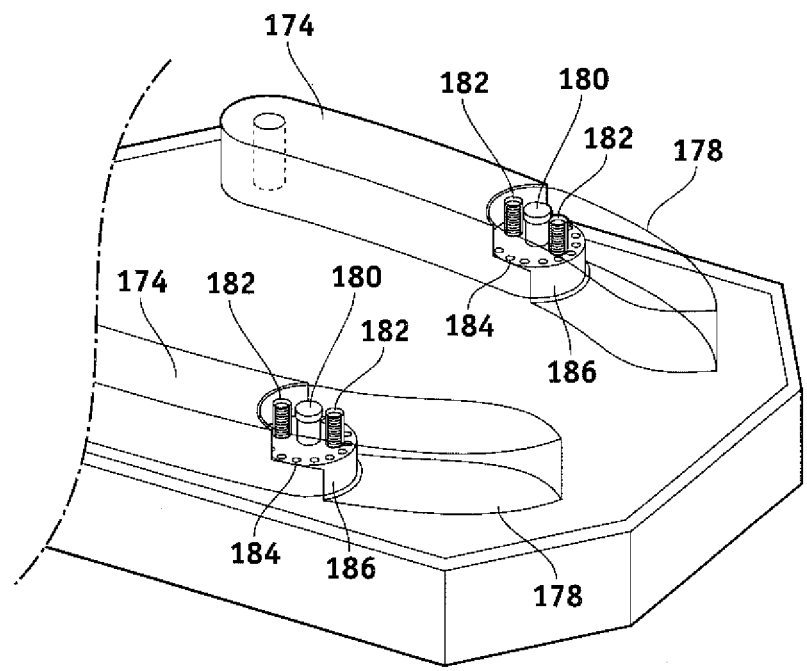

FIGS. 18A and 18B show an alternative foot pedal control treadle 170 having articulated laterally-adjustable guides 172. Each of the guides 172 includes a first segment 174 pivotally mounted to a treadle 176, and a second segment 178 pivotally mounted to the first segment 174. In the illustrated embodiment, the first segments 174 are mounted to rotate at about a midpoint of the anterior/posterior dimension of the treadle 176 and extend in an anterior direction, while the second segments 178 extend farther in an anterior direction. Of course, this orientation could be reversed with the anterior segments 178 mounted to the treadle 176. Indeed, there are numerous possible arrangements of articulated guides with a plurality of adjustable segments, the illustrated embodiment being necessarily representative.

As with the earlier-described guides 80, the combination of the first and second adjustable segments 174, 178 defines an S-shape with both convex and concave regions on their inner faces that conform to different areas of users' feet. In addition, because of the separately pivotal segments 174, 178, an even greater range of adjustment is possible.

In one embodiment, each of the first and second adjustable segments 174, 178 rotates about a pivot point and may be locked in a plurality of different angular rotations. For example, FIG. 18B shows each second adjustable segment 178 in phantom to illustrate a pivot shaft 180 as well as two stop pins 182. The stop pins 182 may be spring-biased toward a plurality of depressions 184 formed in a circular array on flanges 186 of the corresponding first adjustable segment 174. In this way, each second adjustable segment 178 may be incrementally rotated about the pivot shaft 180 with the stop pins 182 falling into the depressions 184 and nominally holding the second adjustable segment relative to the first adjustable segment 174. Although the force required to rotate the second adjustable segment 178 is relatively small it may be sufficient as the user's foot typically presses down on the (rubber-lined) treadle 176, creating friction, and thus does not apply large lateral forces against the guides 172. However, other arrangements that provide more positive locks to the positions of the first and second adjustable segments 174, 178 may be utilized. For example, the mechanism may require the user to press axially downward on the respective segments to unlock them for rotation.

Figure 19:
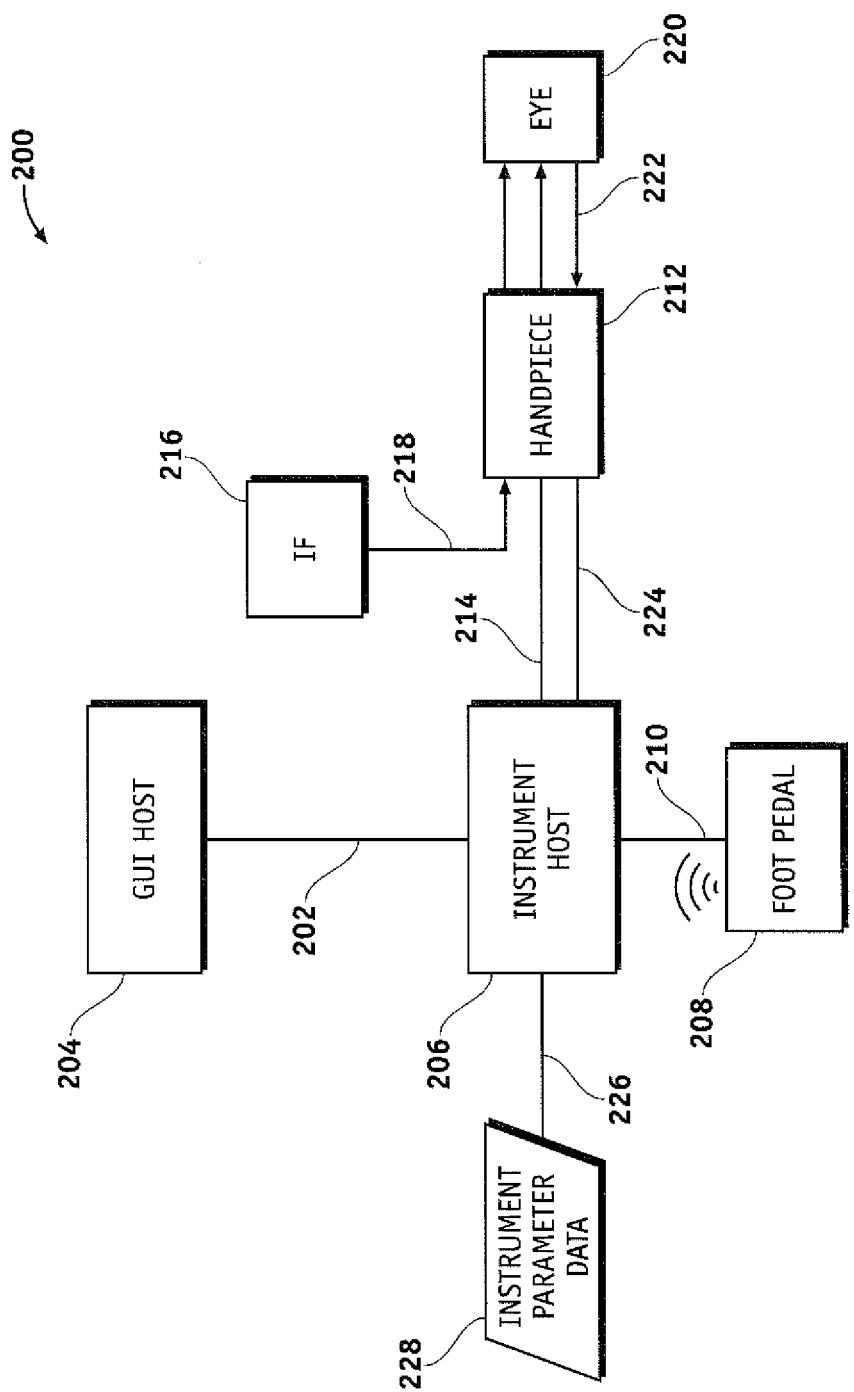
FIG. 19 illustrates an exemplary phacoemulsification/vitrectomy irrigation/aspiration system in a functional block diagram as an exemplary surgical system in which the foot pedal control disclosed herein may be utilized.

While the present foot pedal control may be used in various environments and applications, a particularly useful application is in an ocular surgical system such as a phacoemulsification/vitrectomy system. For instance, FIG. 19 illustrates an exemplary phacoemulsification/vitrectomy system 200 in a functional block diagram to show the components and interfaces for a safety critical medical instrument system in which the foot pedal control disclosed herein may be utilized.

A serial communication cable 202 connects a graphical user interface (GUI) host 204 and instrument host 206 for the purposes of controlling the surgical instrument host 206 by the GUI host 204. The instrument host 206 may be considered a computational device in the arrangement shown, but other arrangements are possible. A switch module associated with an exemplary foot pedal 208, such as described herein, transmits control signals relating internal physical and virtual switch position information as input to the instrument host 206 over a serial communications cable 210, or wirelessly if desired. Instrument host 206 may provide a database file system for storing configuration parameter values, programs, and other data saved in a storage device (not shown). In addition, the database file system may be realized on the GUI host 204 or any other subsystem (not shown) that could accommodate such a file system.

The system 200 has a hand-held operative tip 212 that typically includes a needle and electrical means, such as a piezoelectric crystal, for ultrasonically vibrating the needle. The instrument host 206 supplies power on line 214 to the operative tip 212. An irrigation fluid source 216 can be fluidly coupled to operative tip 212 through line 218. The irrigation fluid and ultrasonic power are applied by the operative tip 212 to an eye 220, or other affected area or region. Alternatively, the irrigation source may be routed to the eye 220 through a separate pathway independent of the handpiece. Aspiration is provided to the eye 220 by one or more pumps (not shown), such as a peristaltic pump and/or venturi pump, via the instrument host 206, through lines 222 and 224. A surgeon/operator may select an amplitude of electrical pulses either using the handpiece, via the instrument host and GUI host, using the foot pedal, and/or voice command.

An interface communications cable 226 connects to the instrument host 206 for distributing instrument sensor/parameter data 228, and may include distribution of instrument settings and parameter information, to other systems, subsystems and modules within and external to instrument host 206. Although shown connected to the instrument host 206, interface communications cable 226 may be connected or realized on any other subsystem (not shown) that could accommodate such an interface device able to distribute the respective data.

While the invention has been described in its preferred embodiments, it is to be understood that the words which have been used are words of description and not of limitation. Therefore, changes may be made within the appended claims without departing from the true scope of the invention.

What is claimed is:

1. A foot pedal control for a surgical system, comprising:
    a base;
    a treadle mounted on the base, wherein the treadle is configured for pitch movement relative to the base, and wherein the treadle having a generally planar foot platform;
    a sensor that tracks the pitch movement of the treadle and generates an electronic signal therefor; and
    a pair of guides mounted on the treadle such that the pair of guides are connected to the treadle by angled guide slots in the treadle, wherein the pair of guides flank and extend upward from the foot platform of the treadle, at least one of the guides being translatable along the angled guide slots to adjust the lateral spacing therebetween and accommodate variable foot widths on the foot platform therebetween.

2. The foot pedal control of claim 1, wherein both of the guides are adjustable.

3. The foot pedal control of claim 2, wherein both of the guides are also adjustable in an anterior-posterior direction.

4. The foot pedal control of claim 1, wherein the angled slot extends from a posterior point outward in an anterior direction at an angle of between about 15° and 45° from the longitudinal axis of the treadle.

5. The foot pedal control of claim 1, wherein the guide is configured to move along the angled slot in a ratcheted fashion so as to have a series of stop positions distinguished by audible and/or tactile clicks.

6. The foot pedal control of claim 1, wherein the guides have a rail extending upward to a height generally perpendicular to the foot platform of between about 15 mm or 0.6 inches and 38 mm or 1.5 inches.

7. The foot pedal control of claim 1, wherein the guides are elongated in an anterior-posterior direction and each includes a lip extending toward the other guide and generally parallel to the foot platform, and a rail extending upward from the lip generally perpendicular to the foot platform.

8. The foot pedal control of claim 1, wherein the guides are elongated in an anterior-posterior direction and S-shaped so as to have convex and concave inner faces to conform to different areas of users' feet.

9. The foot pedal control of claim 1, wherein the treadle further includes a heel stop at the posterior end of the foot platform, the heel stop being convertible from a first position extending upward from the foot platform and a second position at or below the level of the foot platform.

10. A system for surgery, comprising:
    a surgery unit including a hand-held operative tip connected to a console; and
    a foot pedal control in electronic communication with the console, including a base and a treadle mounted on the base, wherein the treadle is configured for pitch movement relative to the base, wherein the treadle having a generally planar foot platform, the foot pedal control having a built-in sensor that tracks the pitch movement of the treadle and generates an electronic signal for communication to the console and subsequent control of the operative tip, the treadle having a pair of guides mounted on the treadle such that the pair of guides are connected to the treadle by angled guide slots in the treadle, and wherein the pair of guides flank and extend upward from the foot platform of the treadle, at least one of the guides being translatable along the angled guide slots to adjust the lateral spacing therebetween and accommodate variable foot widths on the foot platform therebetween.

11. The system of claim 10, wherein the surgery unit is for ophthalmic surgery and the operative tip is adapted for insertion into an eye and includes a lumen for aspiration.

12. The system of claim 10, wherein both of the guides are adjustable.

13. The system of claim 10, wherein both of the guides are also adjustable in an anterior-posterior direction.

14. The system of claim 10, wherein the guides are configured to move in a ratcheted fashion so as to have a series of stop positions distinguished by audible and/or tactile clicks.

15. The system of claim 10, wherein the guides are elongated in an anterior-posterior direction and each includes a lip extending toward the other guide and generally parallel to the foot platform, and a rail extending upward from the lip generally perpendicular to the foot platform.

16. The system of claim 10, wherein the guides are elongated in an anterior-posterior direction and curved with a convex-inward posterior segment and a concave-inward anterior segment.

17. The system of claim 10, wherein the treadle further includes a heel stop at the posterior end of the foot platform, the heel stop being convertible from a first position extending upward from the foot platform and a second position at or below the level of the foot platform.

* * * * *